(12) United States Patent
Catani et al.

(10) Patent No.: US 6,998,480 B2
(45) Date of Patent: Feb. 14, 2006

(54) PROCESS FOR IMPROVING SUCRALOSE PURITY AND YIELD

(75) Inventors: Steven J. Catani, Athens, GA (US); James E. Wiley, Daphne, AL (US); Nicholas M. Vernon, Daphne, AL (US); Carolyn M. Merkel, North Haledon, NJ (US); Edward Micinski, Martinez, GA (US)

(73) Assignee: Tate & Lyle Public Limited Company, London (GB)

(*) Notice: Subject to any disclaimer, the term of this patent is extended or adjusted under 35 U.S.C. 154(b) by 99 days.

(21) Appl. No.: 10/092,730

(22) Filed: Mar. 8, 2002

(65) Prior Publication Data

US 2003/0171575 A1    Sep. 11, 2003

(51) Int. Cl.
C07H 13/02    (2006.01)
(52) U.S. Cl. .......................... 536/124; 514/53
(58) Field of Classification Search ................ 536/4.1, 536/124, 123.13, 127, 115, 119, 120; 514/53; 426/548
See application file for complete search history.

(56) References Cited

U.S. PATENT DOCUMENTS

| | | | |
|---|---|---|---|
| 4,343,934 A | 8/1982 | Jenner et al. ............. 536/122 |
| 4,362,869 A | 12/1982 | Jenner et al. ............. 536/122 |
| 4,380,476 A | 4/1983 | Mufti et al. .............. 127/46.3 |
| 4,405,654 A | 9/1983 | Lee ........................ 426/658 |
| 4,826,962 A | 5/1989 | Rathbone et al. .......... 536/122 |
| 4,980,463 A | 12/1990 | Walkup et al. ............ 536/124 |
| 5,034,551 A | 7/1991 | Vernon et al. ............. 556/89 |
| 5,128,248 A | 7/1992 | Dordick et al. ............ 435/100 |
| 5,141,860 A | 8/1992 | Bornemann et al. ........ 435/100 |
| 5,270,071 A * | 12/1993 | Sharp et al. .............. 426/577 |
| 5,272,137 A | 12/1993 | Blasé et al. ............... 514/54 |
| 5,298,611 A | 3/1994 | Navia et al. .............. 536/4.1 |
| 5,354,902 A | 10/1994 | Merciadez et al. ......... 562/601 |
| 5,374,659 A | 12/1994 | Gowan, Jr. ............... 514/557 |
| 5,384,311 A * | 1/1995 | Antenucci et al. .......... 514/53 |
| 5,397,588 A | 3/1995 | Antenucci et al. .......... 426/573 |
| 5,409,907 A | 4/1995 | Blasé et al. ............... 514/54 |
| 5,498,709 A * | 3/1996 | Navia et al. .............. 536/124 |
| 5,530,106 A | 6/1996 | Navia et al. .............. 536/4.1 |
| 5,593,696 A | 1/1997 | McNally et al. ........... 424/472 |
| 5,621,005 A | 4/1997 | Gowan, Jr. ............... 514/557 |
| 5,658,919 A | 8/1997 | Ratnaraj et al. ............ 514/269 |
| 5,674,522 A | 10/1997 | Shah et al. ............... 424/439 |
| 5,817,340 A | 10/1998 | Roche et al. .............. 424/470 |
| 5,876,759 A | 3/1999 | Gowan, Jr. ............... 424/494 |
| 5,977,349 A * | 11/1999 | Catani et al. ............. 536/124 |
| 6,080,481 A | 6/2000 | Ochs et al. ............... 428/372 |
| 6,090,401 A | 7/2000 | Gowan, Jr. et al. ........ 424/439 |
| 6,211,246 B1 | 4/2001 | Gelotte et al. ............ 514/653 |
| 6,258,381 B1 | 7/2001 | Luber et al. .............. 424/464 |
| 6,277,409 B1 | 8/2001 | Luber et al. .............. 424/476 |
| 6,423,358 B1 * | 7/2002 | Barndt et al. ............. 426/548 |

FOREIGN PATENT DOCUMENTS

| | | |
|---|---|---|
| CA | 2205535 | 9/1994 |
| GB | 2 065 646 A | 7/1981 |

OTHER PUBLICATIONS

R. E. Wingard, Jr., S. Ng, J. A. Dale, and P. C. Wang, Semipreparative High-Pressure Liquid Chromatography of Synthetic Carbohydrates, Journal of Liquid Chromatography 1(6), 775-782 (1978).
International Search Report Jun. 24, 2003.
Butler, Jennifer A., "1992 Sucralose Testing Summary", Nov. 23, 1992, McNeil Specialy Products Company, 24 pages.
1992 Sucralose Summary, printed on Apr. 27, 1992, 28 pages.

* cited by examiner

*Primary Examiner*—James O. Wilson
*Assistant Examiner*—Ganapathy Krishnan
(74) *Attorney, Agent, or Firm*—RatnerPrestia

(57) ABSTRACT

This invention relates to processes for purifying sucralose by the use of an initial non-crystallization purification procedure followed by three or more sequential crystallization steps and recycle of the mother liquor remaining from each crystallization step to the feed of another crystallization or purification step. This invention also relates to sucralose compositions as well as compositions comprising the sucralose compositions of the present invention. These compositions may be highly pure and have a superior taste profile.

6 Claims, 12 Drawing Sheets

|  | A | B | C | D | E | F | G |
|---|---|---|---|---|---|---|---|
| 1 | Effect of various factors on the recovery of sucralose in crystallization schemes | | | | | | |
| 2 | | | 1 Recrystallization | | 3 Recrystallizations | | |
| 3 | Purge of Impurities prior to Crystallization | | None | 50% | None | 50% | 75% |
| 4 | | | Sucralose Recovery | | | | |
| 5 | | 1st Crystallizer | 35% | 43% | 35% | 43% | 50% |
| 6 | | 1st Recrystallizer | 37% | 45% | 38% | 46% | 52% |
| 7 | | 2nd Recyrstallizer | | | 52% | 57% | 59% |
| 8 | | 3rd Recyrstallizer | | | 58% | 59% | 60% |
| 9 | | | Sucralose Flow | | | | |
| 10 | | | | | | | |
| 11 | Total feed to system | | 100 | 100 | 100 | 100 | 100 |
| 12 | 1st Crystallizer | | | | | | |
| 13 | | Total Feed | 128 | 131 | 140 | 146 | 150 |
| 14 | | Crystals Produced | 45 | 57 | 49 | 63 | 75 |
| 15 | | Mother Liquor | 83 | 74 | 91 | 83 | 75 |
| 16 | 1st Recrystallizer | | | | | | |
| 17 | | Total Feed | 45 | 57 | 64 | 86 | 105 |
| 18 | | Crystals Produced | 17 | 26 | 24 | 40 | 55 |
| 19 | | Mother Liquor | 28 | 31 | 40 | 46 | 50 |
| 20 | 2nd Recrystallizer | | | | | | |
| 21 | | Total Feed | | | 31 | 51 | 71 |
| 22 | | Crystals Produced | | | 16 | 29 | 42 |
| 23 | | Mother Liquor | | | 15 | 22 | 30 |
| 24 | 3rd Recrystalizer | | | | | | |
| 25 | | Total Feed | | | 16 | 29 | 42 |
| 26 | | Crystals Produced | | | 9 | 17 | 25 |
| 27 | | Mother Liquor | | | 7 | 12 | 17 |
| 28 | Overall recovery of sucralose | | 17% | 26% | 9% | 17% | 25% |
| 29 | | | | 155% | | 186% | |
| 30 | | | Impurity Flow | | | | |
| 31 | Total feed to system | | 100 | 50 | 100 | 50 | 25 |
| 32 | 1st Crystallizer | | | | | | |
| 33 | | Total Feed | 110 | 55 | 111 | 56 | 28 |
| 34 | | Impurities in Crystals | 11 | 5 | 11 | 6 | 3 |
| 35 | | Mother Liquor | 99 | 49 | 100 | 50 | 25 |
| 36 | 1st Recrystallizer | | | | | | |
| 37 | | Total Feed | 11 | 5 | 12 | 6 | 3 |
| 38 | | Impurtities in Crystals | 1 | 1 | 1 | 1 | 0 |
| 39 | | Mother Liquor | 10 | 5 | 11 | 6 | 3 |
| 40 | 2nd Recrystallizer | | | | | | |
| 41 | | Total Feed | | | 1 | 1 | 0 |
| 42 | | Impurtities in Crystals | | | 0 | 0 | 0 |
| 43 | | Mother Liquor | | | 1 | 1 | 0 |
| 44 | 3rd Recrystallizer | | | | | | |
| 45 | | Total Feed | | | 0 | 0 | 0 |
| 46 | | Impurtities in Crystals | | | 0 | 0 | 0 |
| 47 | | Mother Liquor | | | 0 | 0 | 0 |
| 48 | Overall Impurity Removal | | 98.90% | 98.90% | 99.99% | 99.99% | 99.99% |
| 49 | | | Impurity Level in each Crystallizer | | | | |
| 50 | | Feed | 50.00% | 33.33% | 50.00% | 33.33% | 20.00% |
| 51 | | 1st Crystallizer | 46.13% | 29.53% | 44.32% | 27.56% | 15.62% |
| 52 | | 1st Recrystallizer | 19.66% | 8.82% | 16.22% | 6.72% | 2.86% |
| 53 | | 2nd Recrystallizer | | | 4.21% | 1.30% | 0.47% |
| 54 | | 3rd Recrystallizer | | | 0.84% | 0.23% | 0.08% |
| 55 | | Base Yield | | | | | |

Figure 1

| | A | B | C | D | E | F |
|---|---|---|---|---|---|---|
| 1 | Effect of various factors on the recovery of sucralose in crystallization | | | | | |
| 2 | schemes w/ Recrystallization of 1st Crystallizer Mother Liquour | | | | | |
| 3 | Impurity Purge Prior to Crystalization | | | None | 50% | 75% |
| 4 | | | | Sucralose Recovery | | |
| 5 | | 1st Crystallizer | | 40% | 49% | 54% |
| 6 | | 1st Recrystallizer | | 54% | 58% | 59% |
| 7 | | 2nd Recrystallizer | | 59% | 60% | 60% |
| 8 | | 3rd Recrystallizer | | 60% | 60% | 60% |
| 9 | | 1st m/l Recrystallization | | 35% | 43% | 49% |
| 10 | | | | Sucralose Flow | | |
| 11 | Total feed to system | | | 100 | 100 | 100 |
| 12 | 1st Crystallizer | | | | | |
| 13 | | Total Feed | | 189 | 207 | 221 |
| 14 | | Crystals Produced | | 76 | 100 | 119 |
| 15 | | Mother Liquor | | 113 | 106 | 102 |
| 16 | 1st Recrystallizer | | | | | |
| 17 | | Total Feed | | 113 | 106 | 102 |
| 18 | | Crystals Produced | | 40 | 46 | 50 |
| 19 | | Mother Liquor | | 73 | 61 | 52 |
| 20 | 2nd Recrystallizer | | | | | |
| 21 | | Total Feed | | 107 | 144 | 173 |
| 22 | | Crystals Produced | | 58 | 83 | 102 |
| 23 | | Mother Liquor | | 49 | 61 | 71 |
| 24 | 3rd Recrystallizer | | | | | |
| 25 | | Total Feed | | 76 | 110 | 134 |
| 26 | | Crystals Produced | | 45 | 65 | 80 |
| 27 | | Mother Liquor | | 31 | 44 | 54 |
| 28 | 1st M/L Recrystallizer | | | | | |
| 29 | | Total Feed | | 45 | 65 | 80 |
| 30 | | Crystals Produced | | 27 | 39 | 48 |
| 31 | | Mother Liquor | | 18 | 26 | 32 |
| 32 | Overall recovery of sucralose | | | 27% | 39% | 48% |
| 33 | | | | Impurity Flow | | |
| 34 | Total feed to system | | | 100 | 50 | 25 |
| 35 | 1st Crystallizer | | | | | |
| 36 | | Total Feed | | 123 | 62 | 31 |
| 37 | | Crystals Produced | | 12 | 6 | 3 |
| 38 | | Mother Liquor | | 111 | 56 | 28 |
| 39 | 1st Recrystallizer | | | | | |
| 40 | | Total Feed | | 111 | 56 | 28 |
| 41 | | Crystals Produced | | 11 | 6 | 3 |
| 42 | | Mother Liquor | | 100 | 50 | 25 |
| 43 | 2nd Recrystallizer | | | | | |
| 44 | | Total Feed | | | | |
| 45 | | Crystals Produced | | 14 | 7 | 3 |
| 46 | | Mother Liquor | | 1 | 1 | 0 |
| 47 | 3rd Recrystallizer | | | 12 | 6 | 3 |
| 48 | | Total Feed | | | | |
| 49 | | Crystals Produced | | 2 | 1 | 0 |
| 50 | | Mother Liquor | | 0 | 0 | 0 |
| 51 | 1st M/L Recrystallizer | | | 1 | 1 | 0 |
| 52 | | Total Feed | | | | |
| 53 | | Crystals Produced | | 0 | 0 | 0 |
| 54 | | Mother Liquor | | 0 | 0 | 0 |
| 55 | | m/l | | 0 | 0 | 0 |
| 56 | | | | Impurity Level in each Crystallizer | | |
| 57 | | Feed | | 50.00% | 33.33% | 20.00% |
| 58 | | 1st Crystallizer | | 39.56% | 23.00% | 12.24% |
| 59 | | 1st M/L Recrystallizer | | 49.64% | 34.30% | 21.39% |
| 60 | | 1st Recrystallizer | | 11.34% | 4.53% | 1.94% |
| 61 | | 2nd Recrystallizer | | 1.94% | 0.68% | 0.28% |
| 62 | | 3rd Recrystallizer | | 0.33% | 0.12% | 0.05% |

Figure 2

| | A | B | C | D | E | F | G | H | I | J | K |
|---|---|---|---|---|---|---|---|---|---|---|---|
| 1 | Effect of required purity on yield and the improvements seen with impurity pre-purge | | | | | | | | | | |
| 2 | | | | one recrystallization | | three recrystallizations | | five recrystallizations | | five recrystallizations and re-crop | |
| 3 | | | | Sucralose Recovery | | | | | | | |
| 4 | Purge of Impurities prior to Crystallization | | | None | 50% | None | 50% | None | 50% | None | 50% |
| 5 | | 1st Crystallizer | | 36% | 44% | 36% | 45% | 37% | 45% | 38% | 47% |
| 6 | | 1st Recrystallizer | | 43% | 51% | 45% | 53% | 45% | 53% | 47% | 55% |
| 7 | | 2nd Recrystallizer | | | | 52% | 57% | 53% | 58% | 55% | 58% |
| 8 | | 3rd Recrystallizer | | | | 57% | 59% | 58% | 59% | 58% | 59% |
| 9 | | 4th Recrystallizer | | | | | | 60% | 60% | 59% | 60% |
| 10 | | 5th Recrystallizer | | | | | | 60% | 60% | 60% | 60% |
| 11 | | 1st Re-Crop | | | | | | | | 35% | 43% |
| 12 | | Purity | | 80.08% | 92.36% | 97.59% | 99.31% | 99.83% | 99.95% | 99.87% | 99.96% |
| 13 | | Overall Yield | | 19% | 29% | 12% | 21% | 10% | 19% | 18% | 32% |
| 14 | | Yield Improvement w/ purge | | | 150% | | 178% | | 184% | | 180% |
| 15 | | | | one recrystallization | | three recrystallizations | | five recrystallizations | | five recrystallizations and re-crop | |
| 16 | Purge of Impurities prior to Crystallization | | | None | 50% | None | 50% | None | 50% | None | 50% |
| 17 | | | | Sucralose Flow | | | | | | | |
| 18 | Total feed to system | | | 100 | 100 | 100 | 100 | 100 | 100 | 100 | 100 |
| 19 | 1st Crystallizer | | | | | | | | | | |
| 20 | | Total Feed | | 126 | 127 | 138 | 143 | 141 | 147 | 206 | 224 |
| 21 | | Crystals Produced | | 45 | 56 | 50 | 64 | 51 | 66 | 79 | 106 |
| 22 | | Mother Liquor | | 81 | 71 | 88 | 79 | 90 | 81 | 127 | 119 |
| 23 | 1st Recrystallizer | | | | | | | | | | |
| 24 | | Total Feed | | 45 | 56 | 69 | 91 | 75 | 101 | 117 | 162 |
| 25 | | Crystals Produced | | 19 | 29 | 31 | 48 | 34 | 54 | 55 | 88 |
| 26 | | Mother Liquor | | 26 | 27 | 38 | 43 | 41 | 47 | 61 | 73 |
| 27 | 2nd Recrystallizer | | | | | | | | | | |
| 28 | | Total Feed | | | | 40 | 63 | 50 | 82 | 83 | 135 |
| 29 | | Crystals Produced | | | | 21 | 36 | 27 | 47 | 45 | 79 |
| 30 | | Mother Liquor | | | | 19 | 27 | 23 | 35 | 38 | 56 |
| 31 | 3rd Recrystallizer | | | | | | | | | | |
| 32 | | Total Feed | | | | 21 | 36 | 39 | 69 | 66 | 115 |
| 33 | | Crystals Produced | | | | 12 | 21 | 22 | 41 | 38 | 68 |
| 34 | | Mother Liquor | | | | 9 | 15 | 16 | 28 | 28 | 46 |
| 35 | 4th Recrystallizer | | | | | | | | | | |
| 36 | | Total Feed | | | | | | 29 | 54 | 50 | 90 |
| 37 | | Crystals Produced | | | | | | 17 | 32 | 30 | 54 |
| 38 | | Mother Liquor | | | | | | 12 | 21 | 21 | 36 |
| 39 | 5th Recrystallizer | | | | | | | | | | |
| 40 | | Total Feed | | | | | | 17 | 32 | 30 | 54 |
| 41 | | Crystals Produced | | | | | | 10 | 19 | 18 | 32 |
| 42 | | Mother Liquor | | | | | | 7 | 13 | 12 | 21 |
| 43 | 1st Re-crop Recrystallizer | | | | | | | | | | |
| 44 | | Total Feed | | | | | | | | 127 | 119 |
| 45 | | Crystals Produced | | | | | | | | 45 | 51 |
| 46 | | Mother Liquor | | | | | | | | 82 | 68 |
| 47 | Overall recovery of sucralose | | | 19% | 29% | 12% | 21% | 10% | 19% | 18% | 32% |
| 48 | | | | | 150% | | 178% | | 184% | | 180% |

Figure 3a

|   | A | B | C | D | E | F | G | H | I | J | K |
|---|---|---|---|---|---|---|---|---|---|---|---|
|   |   |   |   | one recrystallization | | three recrystallizations | | five recrystallizations | | five recrystallizations and re-crop | |
| 49 |   |   |   |   |   |   |   |   |   |   |   |
| 50 | Purge of Impurities prior to Crystallization | | | None | 50% | None | 50% | None | 50% | None | 50% |
| 51 |   |   |   | Impurity Flow | | | | | | | |
| 52 | Total feed to system | | | 100 | 50 | 100 | 50 | 100 | 50 | 100 | 50 |
| 53 | 1st Crystallizer | | | | | | | | | | |
| 54 |   | Total Feed | | 119 | 60 | 125 | 62 | 125 | 62 | 156 | 78 |
| 55 |   | Impurities in Crystals | | 24 | 12 | 25 | 12 | 25 | 12 | 31 | 16 |
| 56 |   | Mother Liquor | | 95 | 48 | 100 | 50 | 100 | 50 | 125 | 62 |
| 57 | 1st Recrystallizer | | | | | | | | | | |
| 58 |   | Total Feed | | 24 | 12 | 31 | 15 | 31 | 16 | 39 | 20 |
| 59 |   | Impurities in Crystals | | 5 | 2 | 6 | 3 | 6 | 3 | 8 | 4 |
| 60 |   | Mother Liquor | | 19 | 10 | 25 | 12 | 25 | 12 | 31 | 16 |
| 61 | 2nd Recrystallizer | | | | | | | | | | |
| 62 |   | Total Feed | | | | 7 | 4 | 8 | 4 | 10 | 5 |
| 63 |   | Impurities in Crystals | | | | 1 | 1 | 2 | 1 | 2 | 1 |
| 64 |   | Mother Liquor | | | | 6 | 3 | 6 | 3 | 8 | 4 |
| 65 | 3rd Recrystallizer | | | | | | | | | | |
| 66 |   | Total Feed | | | | 1 | 1 | 2 | 1 | 2 | 1 |
| 67 |   | Impurities in Crystals | | | | 0 | 0 | 0 | 0 | 0 | 0 |
| 68 |   | Mother Liquor | | | | 1 | 1 | 2 | 1 | 2 | 1 |
| 69 | 4th Recrystallizer | | | | | | | | | | |
| 70 |   | Total Feed | | | | | | 0 | 0 | 1 | 0 |
| 71 |   | Impurities in Crystals | | | | | | 0 | 0 | 0 | 0 |
| 72 |   | Mother Liquor | | | | | | 0 | 0 | 0 | 0 |
| 73 | 5th Recrystallizer | | | | | | | | | | |
| 74 |   | Total Feed | | | | | | 0 | 0 | 0 | 0 |
| 75 |   | Impurities in Crystals | | | | | | 0 | 0 | 0 | 0 |
| 76 |   | Mother Liquor | | | | | | 0 | 0 | 0 | 0 |
| 77 | 1st recrop | | | | | | | | | | |
| 78 |   | Total Feed | | | | | | | | 125 | 62 |
| 79 |   | Impurities in Crystals | | | | | | | | 25 | 12 |
| 80 |   | Mother Liquor | | | | | | | | 100 | 50 |
| 81 | Overall Impurity Removal | | | 95.238% | 95.238% | 99.707% | 99.707% | 99.982% | 99.982% | 99.977% | 99.977% |
|   |   |   |   | one recrystallization | | three recrystallizations | | five recrystallizations | | five recrystallizations and re-crop | |
| 82 |   |   |   |   |   |   |   |   |   |   |   |
| 83 | Purge of Impurities prior to Crystallization | | | None | 50% | None | 50% | None | 50% | None | 50% |
| 84 |   |   |   | Impurity Level in each Crystallizer | | | | | | | |
| 85 |   | Feed | | 50.00% | 33.33% | 50.00% | 33.33% | 50.00% | 33.33% | 50.00% | 33.33% |
| 86 |   | 1st Crystallizer | | 48.64% | 31.85% | 47.38% | 30.36% | 46.99% | 29.81% | 43.15% | 25.84% |
| 87 |   | 1st Recrystallizer | | 34.67% | 17.50% | 30.75% | 14.49% | 29.40% | 13.40% | 25.07% | 10.76% |
| 88 |   | 2nd Recrystallizer | | | | 15.49% | 5.53% | 13.39% | 4.55% | 10.50% | 3.48% |
| 89 |   | 3rd Recrystallizer | | | | 6.56% | 2.01% | 4.75% | 1.38% | 3.52% | 1.04% |
| 90 |   | 4th Recrystallizer | | | | | | 0.52% | 0.14% | 1.51% | 0.43% |
| 91 |   | 5th Recrystallizer | | | | | | 0.17% | 0.05% | 0.75% | 0.21% |
| 92 |   | recrop feed | | | | | | | | 49.65% | 34.51% |
| 93 |   | Base Yield | | 60% | | | | | | | |
| 94 |   | Effect Factor | | 0.5 | 0.5 | 0.5 | 0.5 | 0.5 | 0.5 | 0.5 | 0.5 |
| 95 |   | 1st Crystallizer | | 35% | 44% | 36% | 45% | 37% | 45% | 38% | 47% |
| 96 |   | 1st Recrystallizer | | 43% | 51% | 45% | 53% | 45% | 53% | 47% | 55% |
| 97 |   | 2nd Recrystallizer | | | | 52% | 57% | 53% | 58% | 55% | 58% |
| 98 |   | 3rd Recrystallizer | | | | 57% | 59% | 58% | 59% | 58% | 59% |
| 99 |   | 4th Recrystallizer | | | | | | 60% | 60% | 59% | 60% |
| 100 |   | 5th Recrystallizer | | | | | | 0.599127 | 60% | 0.596239 | 60% |
| 101 |   | recrop feed | | | | | | | | 0.351764 | 43% |

Figure 3b

| Lot | Impurity in % | | Chlorinated Impurities in % | | | | | | | Ratio | |
|---|---|---|---|---|---|---|---|---|---|---|---|
| | Adjusted Assay | Water | Residue on Ignition | 4,6'-dichloro galacto sucrose | 4,1'-dichloro galacto sucrose | 1',6'-dichloro sucrose | 3,6'-anhydro-4,1-dichloro galacto sucrose | 4,1',6'-trichloro galacto sucrose-6-acetate | 6,1',6'-trichloro sucrose | Unknown chlorinated carbohydrates | All impurities | Chlorinated Impurities |
| SCN412 | 100.65 | 0.06 | <0.01 | 0.01 | <0.01 | <0.01 | <0.01 | <0.01 | <0.01 | <0.01 | 714:1 | 1428:1 |
| SCN401 | 98.94 | 0.07 | <0.01 | 0.01 | 0.01 | <0.01 | 0.01 | <0.01 | <0.01 | <0.01 | 667:1 | 1428:1 |
| SCN398 | 100.59 | 0.07 | <0.01 | 0.01 | <0.01 | <0.01 | <0.01 | <0.01 | <0.01 | <0.01 | 667:1 | 1428:1 |
| SCN376 | 99.66 | 0.08 | <0.01 | 0.03 | <0.01 | <0.01 | <0.01 | <0.01 | <0.01 | <0.01 | 556:1 | 1111:1 |
| SCN363 | 99.83 | 0.06 | <0.01 | 0.02 | <0.01 | <0.01 | <0.01 | <0.01 | <0.01 | <0.01 | 667:1 | 1250:1 |
| SCN0061 | 100.26 | 0.03 | <0.01 | 0.02 | <0.01 | <0.01 | <0.01 | <0.01 | <0.01 | <0.01 | 833:1 | 1250:1 |
| SCN0054 | 99.40 | 0.05 | <0.01 | 0.02 | <0.01 | <0.01 | <0.01 | <0.01 | <0.01 | <0.01 | 714:1 | 1250:1 |
| SCN0048 | 100.24 | 0.07 | <0.01 | 0.02 | <0.01 | <0.01 | <0.01 | <0.01 | <0.01 | <0.01 | 625:1 | 1250:1 |
| SCN0035 | 100.52 | 0.06 | <0.01 | 0.02 | <0.01 | <0.01 | <0.01 | <0.01 | <0.01 | <0.01 | 667:1 | 1428:1 |
| SCN0007 | 99.01 | 0.04 | <0.01 | 0.01 | <0.01 | <0.01 | <0.01 | <0.01 | <0.01 | <0.01 | 833:1 | 1428:1 |

Analysis Profile of Representative Lots

Figure 9

PROCESS FOR IMPROVING SUCRALOSE PURITY AND YIELD

FIELD OF THE INVENTION

This invention relates to processes for purifying sucralose by the use of an initial non-crystallization purification procedure followed by three or more sequential crystallization steps and recycle of the mother liquor remaining from each crystallization step to the feed of another crystallization or purification step. This invention also relates to sucralose compositions as well as compositions comprising the sucralose compositions of the present invention. These compositions may be highly pure and have a superior taste profile.

BACKGROUND OF THE INVENTION

Sucralose, 4,1',6'-trichloro-4,1',6'-trideoxygalactosucrose, a sweetener with a sweetness intensity several hundred times that of sucrose, is derived from sucrose by replacing the hydroxyl groups in the 4, 1', and 6' positions with chlorine. Synthesis of sucralose is technically challenging because of the need to selectively replace specific hydroxyl groups with chlorine atoms, while preserving other hydroxyl groups including a highly reactive primary hydroxyl group. Numerous approaches to this synthesis have been developed. See, e.g., U.S. Pat. Nos. 4,362,869; 4,826,962; 4,980,463; and 5,141,860, which are expressly incorporated by reference herein. However, such approaches typically provide a product that contains varying levels of other chlorinated sugar compounds in addition to sucralose. Although much effort has been directed toward the synthesis of sucralose, the isolation of sucralose in highly pure form from this complex mixture of contaminants heretofore has received relatively little attention. Early reported work typically involved crystallizing sucralose directly from the synthesis mixture, a process that yields a material with high impurity levels. Sucralose is sometimes purified from a synthesis mixture by silica gel chromatography. See, e.g., U.S. Pat. No. 5,128,248, which is expressly incorporated by reference herein. That procedure, due to its use of silica gel, may be ill-suited to large-volume commercial production of highly pure sucralose. In addition, relatively little attention has been focused on other approaches for removing halogenated sugar impurities from sucralose. Efficient removal of these impurities is important because, even at quite low concentrations, they can have an adverse impact on the sweetness, taste, and flavor-modifying properties of sucralose.

One particular problem that decreases the yield and purity of sucralose is the reluctance of sucralose to crystallize under conditions that would result in rapid crystallization of non-substituted sugars in a relatively pure crystal form. In comparison to sucrose solutions, saturated solutions of sucralose crystallize relatively slowly despite the introduction of seed crystals, and the presence of the various di-, tri-, and tetrachlorosucrose derivatives further interferes with the formation of pure sucralose crystals.

A second problem associated with sucralose purification is the relatively large amount of sucralose that remains in the solution after sucralose crystallization, which reduces overall yield. This solution, known in the art as the "mother liquor" or "recrop," contains one or more undesirable impurities. A simple mathematical analysis illustrates the poor yield obtained by purification based on iterative crystallizations when recovery of material from the mother liquors is not employed. For example, if 60% of the material in each crystallization step is recovered as crystals, the overall yield of four iterative crystallizations would be 0.6×0.6×0.6×0.6, or less than 13%.

Another problem associated with purity and yield of sucralose relates to the formation of a wide range of related chlorinated carbohydrates during sucralose synthesis, which are only partially removed during purification. These related compounds, or impurities, have varying degrees of sweetness, and can interact with the flavor systems of food and beverage products in adverse ways. Various compendial sources, such as the Food and Drug Codex, the United States Pharmacopoeia, and Joint Expert Committee on Food Additives have established specifications for sucralose. All of these authorities allow impurities in sucralose of up to 2%. Individuals can detect sweetness differences arising from impurities when the impurity level is as low as about 1%, and even lower impurity levels can affect the perceived taste of complex flavor systems. Hence, chlorinated carbohydrates created during sucralose synthesis may have a profound effect on taste, affecting the quality of an end product. Conversely, the removal of impurities may beneficially affect taste, sweetness, and palatability.

Pure sucralose can be made by purifying the blocked or partially blocked sucralose precursors, deblocking the precursors, and then isolating sucralose. Another approach is to deblock the pure sucralose and then purify and isolate the sucralose. Another approach is to partially purify the blocked or partially blocked sucralose precursors, deblock the precursors, and then purify and isolate the sucralose. Therefore, the purification of these precursor compounds is needed to increase the overall yield of subsequent reaction steps.

Sucralose and the blocked or partially blocked sucralose precursors can be purified by crystallization, liquid-liquid extraction, or chromatography. Recrystallization, re-extraction, and further chromatography can be used to enhance purity. Unlike sucrose and most carbohydrates, however, the crystallization of sucralose and the blocked or partially blocked sucralose precursors from crude solutions containing other chlorinated carbohydrates and blocked or partially blocked chlorinated carbohydrates produces crystals that contain significant amounts of these other compounds. This is in marked contrast to the crystallization of sucrose, which results in relatively pure crystals. In all cases the recovery of sucralose and blocked or partially blocked sucralose precursors in the crystallization process is less than 100%, and more typically about 50%, resulting in significant loss of sucralose during purification.

Various methods have been developed related to sucralose extraction. For example, U.S. Pat. No. 4,343,934, expressly incorporated by reference herein, relates to the crystallization of sucralose from an aqueous solution, followed by two cycles of heating the remaining mother liquor, concentrating, adding seed crystals, and cooling. The three cycles of crystallization provided an overall yield of 76.6%. U.S. Pat. No. 4,362,869, expressly incorporated by reference herein, shows 4,1',6'-trichloro-4,1',6'-trideoxygalactosucrose pentaacetate (TOSPA) as a precursor of sucralose in one synthetic route but does not identify impurities or recycle mother liquors.

U.S. Pat. No. 4,380,476, expressly incorporated by reference herein, relates to a process in which TOSPA is purified by three sequential crystallizations, followed by deacylation to yield sucralose, and then a single crystallization of sucralose from the product stream. No pre-crystallization extraction is used, and no recycling of the mother liquor is employed. This process purportedly achieves a purity of 99%; however, the yield of this process is quite low (5%).

U.S. Pat. No. 4,405,654 relates to synthetic routes for synthesizing various halosucrose derivatives and is expressly incorporated by reference herein. The compounds are isolated by ion exchange chromatography or by crystallization from solvents such as diethyl ether, ethyl acetate, and petrol.

U.S. Pat. No. 4,980,463, expressly incorporated by reference herein, relates to various processes for purifying sucralose-6-benzoate, a precursor to sucralose in some synthetic routes, including crystallization followed by recrystallization. Also shown is an extractive crystallization, which combines extraction and a first crystallization in a single step. U.S. Pat. No. 5,298,611, expressly incorporated by reference herein, relates to an extractive purification process during crystallization of the sucralose pentaester. In this procedure, the sucralose pentaester is present in an impure reaction mixture in a solvent such as toluene. Water is added to create a biphasic mixture, which is cooled to induce the crystallization of the sucralose pentaester. The pentaester form is then purified, and sucralose in relatively pure form is recovered by hydrolysis of the ester. The water provides a second phase into which the polar materials are extracted, leading to production of purer sucralose pentaester crystals.

U.S. Pat. No. 5,498,709, expressly incorporated by reference herein, relates to a process in which a crude sucralose reaction mixture is extracted with ethyl acetate in a ROBATEL counter current extractor. The ethyl acetate solution of sucralose is then concentrated to a syrup, dissolved in water, treated with a decolorizing agent, again concentrated to a syrup, and diluted in ethyl acetate. The solution is seeded with sucralose crystals, and crystallization is allowed to proceed for several days.

U.S. Pat. No. 5,530,106, also expressly incorporated by reference herein, relates to a process in which sucralose-6-acetate in a reaction mixture is extracted with ethyl acetate (using either batch extraction or a counter current extraction processes) and then crystallized after being combined with the mother liquor from the second crystallization of a previous batch and the second crop solid from the previous batch. In a second crystallization step, once crystallized sucralose-6-acetate is combined with the mother liquor from the third crystallization of a previous batch and crystallized from a mixture of water and ethyl acetate. A third crystallization is performed by dissolving the twice-crystallized material in a mixture of water and ethyl acetate. This thrice-crystallized material is then deacetylated and purified to yield sucralose.

The preceding discussion identifies an unmet need for a sucralose purification process that produces sucralose compositions of enhanced purity and also minimizes the overall loss of sucralose during the purification process.

SUMMARY OF THE INVENTION

The present invention relates to producing sucralose of high purity and at high yield that comprises an early non-crystallization process step that removes a substantial portion of the impurities present after the completion of synthesis, followed by a process of one or more sequential crystallizations and optional dissolutions, and subsequent recrystallizations. In one embodiment, at least a portion of the mother liquor from one or more crystallization steps is recycled to an earlier crystallization step or to the non-crystallization extraction step. An important discovery is that the recycling of the mother liquor to an earlier crystallization step provides a significant improvement in yield and improves the efficiency of the recrystallization process. This occurs because the mother liquor at each subsequent crystallization generally has lower levels of impurities than the sucralose solutions employed in the earlier crystallizations, resulting in more rapid rates of crystallization and the formation of crystals more pure than would be obtained otherwise.

Additionally, the early non-crystallization extraction step employed removes different impurities than those that are removed by crystallization. Hence the recycling of mother liquors from crystallizations to the non-crystallization extraction step provides a means for efficiently improving purity of sucralose. The combination of these two procedures yields sucralose compositions of greater impurity than has been achieved previously.

One embodiment of the present invention comprises methods for purifying sucralose from a crude sucralose solution comprising the steps of subjecting a crude sucralose solution to a non-crystallization extraction step to yield an increased purity sucralose solution, performing a crystallization procedure on the increased purity sucralose solution to obtain crystalline sucralose and a mother liquor, and recycling at least a portion of the mother liquor to the solution. In this embodiment, the subjecting step may be performed more than once. Additionally, the recycling step can be performed more than once where the subjecting step is performed once, or more than once. The performing step can also be performed at least three times, three times, four times, five times or more than five times, where the subjecting step and recycling steps are performed either once, or more than once. The subjecting step may also be selected from the group consisting of liquid-liquid extraction, extractive precipitation, chromatography, precipitation followed by solvent washing and derivative formation followed by extraction or distillation. This subjecting step may also be carried out either as a batch operation or a continuous operation.

Another embodiment of the present invention comprises methods of purifying sucralose from a crude sucralose solution comprising the steps of subjecting the crude sucralose solution to a non-crystallization purification step to yield an increased purity sucralose solution, performing a crystallization procedure on the crude sucralose solution to obtain crystalline sucralose and a first mother liquor, dissolving the crystalline sucralose to obtain a sucralose solution and performing a crystallization procedure on the sucralose solution to obtain a more pure crystalline sucralose and an additional mother liquor, and recycling the mother liquor obtained from one or more of the crystallization procedures into one or more of the sucralose solutions utilized in the earlier crystallization procedures. In this embodiment, the subjecting step may be performed more than once. The performing step may also be performed at least three times, three times, four times, five times, or more than five times, where the subjecting step is performed either once, or more than once. All of the steps in this embodiment may be performed either as batch operations or continuous operations.

Another embodiment of this invention comprises methods of obtaining sucralose from a feed mixture comprising 6-O-acyl-4,1',6'-trichloro-4,1',6'-trideoxygalactosucrose, other chlorinated sucrose byproducts, and optionally blocked or partially blocked chlorinated sucrose byproducts comprising the steps of performing a non-crystallization extraction step on the feed mixture to obtain an increased purity 6-O-acyl-4,1',6'-trichloro-4,1',6'-trideoxygalactosucrose composition, crystallizing the increased purity 6-O-acyl-4,1',6'-trichloro-4,1',6'-trideoxygalactosucrose composition to obtain 6-O-acyl-4,1',6'-trichloro-4,1',6'-trideoxygalactosucrose and a mother liquor, executing at least three additional sequential crystallizations of the 6-O-acyl-4,1',6'-trichloro-4,1',6'-trideoxygalactosucrose to obtain a substantially pure 6-O-acyl-4,1',6'-trichloro-4,1',6'-trideoxygalactosucrose and additional mother liquor, and converting the substantially pure 6-O-acyl-4,1',6'-trichloro-4,1',6'-trideoxygalactosucrose to substantially pure sucralose. In this embodiment, the crystallizing step may be performed at least three times, three times, four times, five times, or more than five times. Additionally, the performing step may be performed more than once where the crystallizing step is performed at least three times and may be selected from the group consisting of liquid-liquid extraction, chromatography, and precipitation followed by solvent washing. In this embodiment, the mother liquors from one or more of the performing steps or crystallizing steps may be recycled to an earlier performing or crystallizing step.

Also within an embodiment of the present invention are methods of obtaining sucralose from a feed mixture comprising 6-O-acyl-4,1',6'-trichloro-4,1',6'-trideoxygalactosucrose, other chlorinated sucrose byproducts, and optionally other blocked or partially blocked chlorinated sucrose byproducts comprising the steps of performing a non-crystallization extraction step on the feed mixture to obtain an increased purity sucralose precursor stream, converting the 6-O-acyl-4,1',6'-trichloro-4,1',6'-trideoxygalactosucrose in the increased purity sucralose precursor stream to sucralose, and crystallizing the sucralose to obtain a crystalline sucralose and a mother liquor to obtain a substantially pure sucralose and additional mother liquor. In this embodiment, each performing, crystallizing and converting step may be performed more than once. Particularly, the crystallizing step can be performed at least three times, three times, four time, five times, or more than five times. The performing step may be performed once or more than once, where the crystallizing step is performed more than once, or all the steps are performed more than once. In addition, the 6-O-acyl-4,1',6'-trichloro-4,1',6'-trigalactosucrose may be crystallized from the precursor stream prior to converting said 6-O-acyl-4,1',6'-trideoxychloro-4,1',6'-trideoxygalactosucrose to sucralose.

The present invention also includes methods for purifying sucralose from a crude sucralose solution comprising the steps of subjecting a crude sucralose solution to a non-crystallization extraction step to yield an increased purity sucralose solution, performing a crystallization procedure on the increased purity sucralose solution to obtain crystalline sucralose and a mother liquor, recycling at least a portion of the mother liquor to the feedstock utilized in the first step, to yield a final crystalline sucralose composition wherein the level of other chlorinated sugars is less than about 0.2% of the composition by weight. This final crystalline sucralose composition can also be purified in ratios of around 500:1, to around 750:1 and to around 1000:1 sucralose to acylated sucralose, organic or inorganic salt, carbohydrates, or halogenated derivatives. Halogenated sugar derivatives may include dichlorosucrose acetate, 6,1',6'-trichlorosucrose, 4,6,6'-trichlorosucrose, 4,1',4',6'-tetrachlorogalactotagatose, 4,1',6'-trichlorogalactosucrose-6-acetate, and 4,6,1',6'-tetrachlorogalactosucrose, 4,1'-dichlorogalactosucrose, 3',6'-dichloroanhydrosucrose, 4,6'-dichlorogalactosucrose, 1',6'-dichlorosucrose, 6,6'-dichlorosucrose, and 4,1',6'-trichlorosucrose.

Other embodiments of the present invention include aqueous solutions containing the purified sucralose compositions derived from each of the embodiments mentioned above. Additional embodiments of the purified sucralose compositions may contain additional preservatives like sorbic acid, benzoic acid, or dihydroxybenzoic acid, and salts thereof that are suitable for human ingestion. Products including beverages, combination sweeteners, consumer products and sweetener products may also contain the purified sucralose compositions of the present invention. The methods of the present invention are applicable to the purification of compounds other than sucralose. Specifically, these procedures can be similarly used to purify various hydroxyl-substituted trichlorogalactosucrose compounds that, for example, are precursors of sucralose in various sucralose synthetic routes. Additionally, the processes described herein can be used to produce relatively pure preparations of other mono-, di-, tri-, and tetrachlorosucroses, which also have distinct taste properties and can be used to modify the sweetness properties of various comestibles. Also contemplated within the scope of the present invention are sucralose compositions obtained by any one and/or some combination of the methodologies of the present invention as well as products comprising the sucralose compositions obtained by any one and/or some combination of the methodologies of the present invention.

Another embodiment of the present invention relates to methods for enhancing the palatability of a consumer product comprising the step of adding purified sucralose to the consumer product. In one embodiment, the purified sucralose may be 99.9% pure. In another embodiment, the sucralose may be present within the consumer product at a level of about 3 parts per million to about 0.1%. In another embodiment, the sucralose may be present within the consumer product at a level of about 5 parts per million to about 1000 parts per million. In another embodiment, the sucralose may be present within the consumer product at a level of about 10 parts per million to about 500 parts per million.

An additional embodiment of the present invention relates to methods for enhancing the palatability of a beverage comprising the step of adding purified sucralose to the beverage. In one embodiment, the purified sucralose may be 99.9% pure. In another embodiment, the sucralose may be present within the beverage at a level of about 3 parts per million to about 0.1%. In another embodiment, the sucralose may be present within the beverage at a level of about 5 parts per million to about 1000 parts per million. In another embodiment, the sucralose may be present within the beverage at a level of about 10 parts per million to about 500 parts per million.

Another embodiment of the present invention relates to methods for enhancing the palatability of a consumer product comprising the step of adding purified sucralose to a consumer product wherein the level of said sucralose in a resulting consumer product does not modify the sweetness of the resulting consumer product.

An additional embodiment of the present invention relates to methods for enhancing the palatability of a beverage comprising the step of adding purified sucralose to a beverage wherein the level of said sucralose in a resulting beverage does not modify the sweetness of the resulting beverage.

Other objectives, features and advantages of the present invention will become apparent from the following detailed description. The detailed description and the specific examples, although indicating specific embodiments of the invention, are provided by way of illustration only. Accordingly, the present invention also includes those various changes and modifications within the spirit and scope of the invention that may become apparent to those skilled in the art from this detailed description.

BRIEF DESCRIPTION OF THE DRAWINGS

FIG. 1 provides a chart that depicts the effect of various factors on the recovery of sucralose associated with various crystallization processes.

FIG. 2 provides a chart that depicts the effect of various factors on the recovery of sucralose associated with various crystallization processes.

FIGS. 3a and 3b provide a chart that depicts the effect of various factors on the recovery of sucralose associated with various crystallization processes.

FIG. 9 provides a chart of an analysis of the purified sucralose of the present invention.

DETAILED DESCRIPTION OF THE INVENTION

Figure 4:
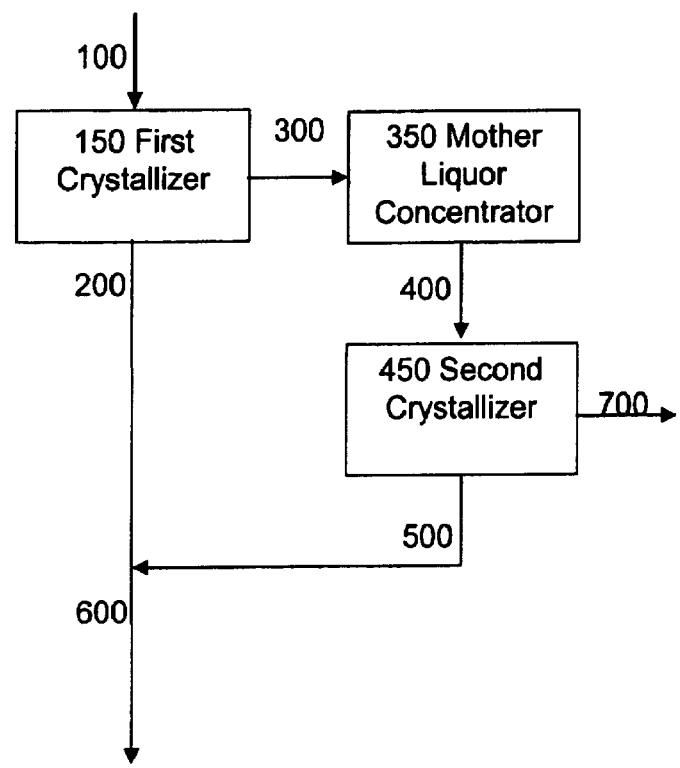
FIG. 4 provides a flowchart of a mother liquor recovery method of concentration followed by recrystallization.

It is understood that the present invention is not limited to the particular methodologies, protocols, solvents, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a solvent" is a reference to one or more solvents and includes equivalents thereof known to those skilled in the art and so forth.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the present invention. All references cited herein are incorporated by reference herein in their entirety.

Definitions

Batch operation: as used herein describes a procedure in which a fixed amount of materials are introduced into a process, and the products obtained from this fixed amount of input are recovered prior to the addition of more input material.

Beverage: as used herein includes any non-carbonated or carbonated beverage such as cola, diet cola, soda, diet soda, juice cocktail, root beer, birch beer, any fountain drink, sparkling fruit juice, water, sparkling water, tonic water, sport drink, and club soda. Beverage may also include any non-alcoholic or alcoholic drink such as any beer, including ale, pilsner, lager, or derivation thereof, malt liquor, red wine, white wine, sparkling wine, fortified wine, wine cooler, wine spritzer, any pre-made cocktail mixer including margarita mix, sour mix, or daiquiri mix, any fermented fruit or tea beverage, hard liquor, and any flavored liqueur such as brandy, schnapps, bitters, or cordial. Beverage may include any dairy, milk, or cream product or any dairy, cream, or milk substitute such as half & half, non-dairy creamer, powdered creamer, flavored creamer, soy milk product, and lactose-free milk product. Beverage may also include any fruit or vegetable juice in whole, concentrated, or powdered form and any combination of fruit and vegetable juices or other beverages. Beverage may also include coffee, any coffee drink, any coffee flavoring syrup, tea, iced tea, and cocoa, as well as any combination of any of the foregoing.

Blocked sucralose: as used herein refers to sucralose molecules on which some or all of the remaining hydroxyl groups have been blocked by esterification or other means.

Combination sweetener: as used herein includes any combination or permutation of sweeteners, including combinations of sucralose, saccharin, aspartame, acesulfame potassium, cyclamate, alitame, stevioside, glucose, fructose, levulose, maltose, lactose, any sugar alcohol, sorbitol, xylitol, and mannitol.

Consumer product: as used herein includes fruit products such as applesauce, jams, jellies, marmalades, fruit snacks, fruit butters, and fruit spreads. Consumer product may also include any dairy, milk, or cream product such as cheese, ice cream, and yogurt. Consumer product includes baked goods such as breads, doughnuts, cakes, cheesecakes, danishes, pastries, pies, bagels, cookies, scones, crackers, muffins, and wafers. Consumer product includes cereal products such as cold cereals, grits, hot cereals, granola mixes, oatmeal, and trail mixes. Consumer product includes condiments such as butter, peanut butter, whipped cream, sour cream, BBQ sauce, chili, syrup, gravy, mayonnaise, olives, seasonings, relish, pickles, sauces, snack dips, ketchup, salsa, mustard, salad dressings, and pickled peppers. Consumer product includes snack foods such as pudding, candy bars, hard candy, chocolate products, lollipops, fruit chews, marshmallows, chewing gum, bubble gum, gummy bears, taffy, pie fillings, syrups, gel snacks, mints, popcorn, chips, and pretzels. Consumer product includes meat products such as hot dogs, canned fish, sausage, prepared meats, canned meat, dehydrated meat, and luncheon meat. Consumer product includes soups, consomme, and bullion. Consumer product includes dental products such as toothpaste, dental floss, mouthwash, denture adhesive, enamel whitener, fluoride treatments, and oral care gels. Consumer product includes cosmetic items such as lipstick, lip balm, lip gloss, and petroleum jelly. Consumer product includes therapeutic items such as non-tobacco snuff, tobacco substitutes, pharmaceutical compositions, chewable medications, cough syrups, throat sprays, throat lozenges, cough drops, antibacterial products, pill coatings, gel caplets, soluble fiber preparations, antacids, tablet cores, rapidly absorbed liquid compositions, stable foam compositions, rapidly disintegrating pharmaceutical dosage forms, beverage concentrates for medicinal purposes, aqueous pharmaceutical suspensions, liquid concentrate compositions, and stabilized sorbic acid solutions. Consumer product includes nutritional products such as meal replacement bars, meal replacement shakes, dietary supplements, protein mixes, protein bars, carbohydrate control bars, low carbohydrate bars, meal supplements, electrolyte solutions, whey protein products, metabolic response modifiers, appetite control beverages, and echinacea sprays. Consumer product includes animal foodstuffs such as dog and cat food, and bird. Consumer product includes foodstuffs such as baby food. Consumer product includes tobacco products such as pipe tobacco, cigarette tobacco, and chewing tobacco.

Continuous operation: as used herein includes procedures in which product may be removed from the process while input may be added; removal of product or addition of input may be incremental, discontinuous, or at a constant rate. Those skilled in the art will readily recognize that the terms "batch operation" and "continuous operation" are somewhat arbitrary, and that many intermediate operations between pure batch operations and pure continuous processes are possible. The embodiments of the present invention may be readily practiced by this full range of possible operations.

Crude sucralose: as used herein includes sucralose mixed with other chlorinated sugars, as well as sucralose and other chlorinated sugars on which some or all of the hydroxyl groups remaining after chlorination may have been blocked by esterification or other means known to those skilled in the art.

Crystallization: as used herein includes processes in which a solution is rendered saturated or supersaturated with respect to a dissolved component, and the formation of crystals of this component is achieved. The initiation of crystal formation may be spontaneous, or it may require the addition of seed crystals. As used herein, crystallization also describes the situation in which a solid or liquid material is dissolved in a solvent to yield a solution which is then rendered saturated or supersaturated so as to obtain crystals. Also, included in the term crystallization are the ancillary processes of washing the crystals with one or more solvents, drying the crystals, and harvesting the final product so obtained.

Extraction operation: as used herein includes procedures that may be performed on a mother liquor to remove impurities from the mother liquor. The specific operation may be selected from any number that may be suitable for removing undesirable impurities. These operations may include, but are not limited to, distillation, solvent extraction, chromatography, and derivatization followed by removal of the derivatized material.

Impurity: as used herein includes compounds other than sucralose and includes products of any number of processes for synthesizing sucralose that are not sucralose. Impurity includes any monochloro-, dichloro-, tetrachloro-, and pentachloro-derivative of sucrose and any other dissacharide derived from sucrose, as well as any trichloro-derivative other than sucralose itself, whether present in free form or as esters of carboxylic acids. Impurity includes any of the halogenated sugar derivatives within Tables 1 through 4, such as dichlorosucrose acetate, 6,1',6'-trichlorosucrose, 4,6, 6'-trichlorosucrose, 4,1',4',6'-tetrachlorogalactotagatose, 4,1',6'-trichlorogalactosucrose-6-acetate, 4,6,1',6'-tetrahlorogalactosucrose, 4,1'-dichlorogalactosucrose, 3',6'-dichloroanhydrosucrose, 4,6'-dichlorogalactosucrose, 1',6'-dichlorosucrose, 6,6'-dichlorosucrose, 4,1',6'-trichlorosucrose, 4,6, 6'-trichlorogalactosucrose, 4,1',5'-trichlorogalactosucrose-6-acetate, and 4,6,6'-trichlorogalactosucrose. Includes any organic or inorganic salt, carbohydrate, or acylated sucralose.

Recycling of a mother liquor: as used herein refers to the practice of adding the mother liquor to another sucralose solution prior to, or during, its crystallization. The mother liquor may be further concentrated or purified prior to recycling. Recovery of a substantial portion of the sucralose remaining in this mother liquor may be essential to achieving an economically acceptable process yield.

Solvent: as used herein includes a liquid that can dissolve another substance.

Sweetener product: as used herein includes any product comprising any combination or permutation of sucralose and/or any other sweeteners, including saccharin, aspartame, acesulfame potassium, cyclamate, alitame, stevioside, glucose, sucrose, fructose, sucrose, levulose, maltose, lactose, any sugar alcohol, sorbitol, xylitol, and mannitol.

Methods of Extraction and Resultant Sucralose Products

One significant challenge in the commercial production of high purity sucralose is the poor yield that accompanies the sequential crystallization and recrystallization of sucralose. As the sucralose obtained by crystallization becomes increasingly pure, the residual mother liquor contains an increasing proportion of sucralose and a decreasing proportion of chlorinated carbohydrate impurities. Thus it is desirable to recover a substantial portion of the sucralose present in the various mother liquors without diminishing the purity of the final product. In one aspect, the present invention seeks to remedy the traditional problems associated with sucralose extraction and/or purification by combining an initial non-crystalline extraction with other processes such as crystalline extraction and recycling of mother liquor. These steps, or processes, may be combined in any order and repeated any number of times. Crystalline extraction is preferably performed at least three times.

One aspect of this invention involves methods for efficiently recovering the sucralose present in the mother liquors while limiting the reincorporation of impurities from the mother liquors into the final purified sucralose product. In the methods of the present invention, the typical chlorinated sucrose mixture may contain a mixture of compounds as, for example, described in U.S. Pat. No. 5,977,349, which is expressly incorporated herein by reference. The types of compounds present in this chlorinated mixture may vary according to the synthetic route used, and the particular conditions of the synthesis. Table 1 below shows the levels of sucralose and several impurities in representative material obtained by the synthetic procedure that may precede the purification procedure described in this disclosure. Such procedures are readily available and known to those in the art. Indeed, one may specifically employ the extractive methodologies as disclosed in U.S. Provisional Patent Application entitled "Extractive Methods for Purifying Sucralose" filed on even date herewith. This invention is broadly applicable, and is not constrained by the particular profile of impurities that result from a synthetic route. Generally, sucralose may comprise at least 40% by weight of all of the sucrose derivatives in the crude sucralose composition. The chlorinated mixture may be a solid material, or it may be a solution in water or other acceptable solvent. If the chlorinated mixture is solid, it is preferably converted to a solution prior to its purification in the process described herein.

TABLE 1

Representative Crude Sucralose Composition

| Component | Composition (% by Weight of Solution) |
|---|---|
| Sucralose | 3.252 |
| 4,1'-dichlorogalactosucrose | 0.138 |
| 3',6'-anhydrogalactosucrose | 0.165 |
| 4,6'-dichlorogalactosucrose | 1.115 |
| 1',6'-dichloroscurose | 0.394 |
| 6,6'-dichlorosucrose | 0.075 |
| 4,1',6'-trichlorosucrose | 0.079 |
| 6,1',6'-trichlorogalactosucrose | 0.302 |
| 4,6,6'-trichlorosucrose | 0.273 |
| 4,1',4',6'-tetrachlorogalactotagatose | 0.110 |
| 4,1',6'-trichlorogalactosucrose-6-acetate | 0.030 |
| 4,6,1',6'-tetrachlorogalactosucrose | 0.410 |

One aspect of the present invention seeks to remove impurities that interfere with crystallization through sucralose purification by a non-crystallization extraction step, crystallization extraction and recycling of mother liquor, and vice versa. Therefore, as described in detail below, the use of multiple crystallizations accompanied by mother liquor recycle steps may produce a sucralose composition that is purer than any previously reported, while maintaining the high overall yield important for a commercial process.

The individual process steps described in this invention may generally be carried out as batch operations or continuous operations and may include one or more extraction and/or crystallization steps. By combining extraction and crystallization, undesirable chlorinated carbohydrates or undesirable blocked or partially blocked chlorinated carbohydrates may be removed to increase the purity of sucralose. Combining extraction with crystallization may also yield a high recovery of sucralose.

Non-Crystallization Purification

In one embodiment, the present invention may comprise an initial non-crystallization purification of a crude sucralose solution to reduce the level of impurities in the solution. Solvent extraction, for example, may be used in this aspect of the present invention. Other alternatives may also be used, including chromatography, precipitation with or without an anti-solvent followed by washing, or formation of derivatives followed by extraction or distillation, such as those disclosed in U.S. Pat. Nos. 4,980,463; 5,034,551; 5,498,709; 5,498,709; 5,498,709; 5,530,106; and U.S. Provisional Application entitled "Extractive Methods for Purifying Sucralose," which are expressly incorporated by reference herein.

In a solvent extraction approach, a wide range of extraction solvents may be used, including, but not limited to, n-pentane, n-hexane, Freon® TF, n-heptane, diethyl ether, 1,1,1 trichloroethane, n-dodecane, white spirit, turpentine, cyclohexane, amyl acetate, carbon tetrachloride, xylene, ethyl acetate, toluene, tetrahydrofuran, benzene, chloroform, trichloroethylene, Cellosolve® acetate, methyl ethyl ketone, acetone, diacetone alcohol, ethylene dichloride, methylene chloride, butyl Cellosolve®, pyridine, Cellsolve®, morpholine, dimethylformamide, n-propyl alcohol, ethyl alcohol, dimethyl sulphoxide, n-butyl alcohol, methyl alcohol, propylene glycol, ethylene glycol, glycerol, and water. The solvents preferably allow the formation of two separable phases that may preferably exhibit differing solubilities for sucralose and other unwanted chlorinated carbohydrates. In a specific embodiment, an ethyl acetate and water system may be used for extraction. This solvent combination may provide a good extraction in addition to the low cost and favorable safety profiles of the solvents used. A wide range of extraction equipment may be used in this approach, ranging from batch mixer-settlers to continuous multistage countercurrent extractors. In a preferred embodiment the ratio of ethyl acetate to water may be about 3:1.

FIG. 1 shows the effect of various factors on the recovery in each crystallization and on overall recovery, particularly the overall effect of purging impurities prior to crystallization. In order to achieve high yield and low impurities, impurities may be purged before crystallization.

Referring to FIG. 1, 100 pounds of sucralose is fed to the system (col. C, line 11) along with 100 pounds of impurities (col. C, line 31). No impurities are purged prior to the first crystallization.

After the first crystallization, 45 pounds of crystals are produced (col. C, line 14) and 83 pounds of mother liquor are produced (col. C, line 15). The mother liquor is purged from the system.

Next, the crystals from the first crystallization are recrystallized. The total feed to the recrystallizer is 45 pounds (col. C, line 17), which was produced by the first crystallization. The recrystallization yields 17 pounds of sucralose crystals (col. C, line 18) and 28 pounds of mother liquor (col. C, line 19). The mother liquor is recycled and the total feed to the system at a steady-state equilibrium is 128 pounds (col. C, line 13). This entire process yields 17 pounds of sucralose or 17% of the feed to the system (col. C, line 28).

This same process is also analyzed by impurity removal in FIG. 1. As stated previously, 100 pounds of impurities are initially present in the system (col. C, line 31). No impurities are purged prior to crystallization. After the first crystallization, there are 11 pounds of impurities left in the crystals (col. C, line 35) and 99 pounds of mother liquor (col. C, line 35). The mother liquor is purged from the system.

Next, the crystals and impurities from the first crystallization are recrystallized. The total feed to the system is 11 pounds of crystals and impurities (col. C, line 37), which was produced by the first crystallization. The recrystallization yields 1 pound of impurity in the crystals (col. C, line 38) and 10 pounds of mother liquor (col. C, line 39). The mother liquor is recycled and the total feed is 110 pounds (col. C, line 33). The overall impurity removal is 98.90% (col. C. line 48). Hence, although most of the impurities are removed from the initial feed, the sucralose yield is very low.

In contrast, if impurities are purged prior to the first crystallization, the sucralose yield may be increased. Referring again to FIG. 1, col. D, one-half of the impurities may be purged from the system by one or more of the extraction methods described above. In this example, 100 pounds of sucralose are fed to the system (col. D, line 11) and 50 pounds of impurities are fed to the system (col. D, line 31).

After the first crystallization, 57 pounds of crystals are produced (col. D, line 14) and 74 pounds of mother liquor are produced (col. D, line 15). The mother liquor is purged from the system.

Next, the crystals from the first crystallization are recrystallized. The total feed to the recrystallizer is 57 pounds (col. D, line 17), which was produced by the first crystallization. The recrystallization yields 26 pounds of sucralose crystals (col. D, line 18) and 31 pounds of mother liquor (col. D, line 19). The mother liquor is recycled and the total feed is 131 pounds (col. D, line 13). This entire process yields 26 pounds of sucralose or 26% of the feed to the system (col. C, line 28), which is a significantly higher yield than when impurities are not purged prior to crystallization and is an improvement of 155% over the process without an impurity purge (col. D, line 29).

This same process is also analyzed by impurity removal in FIG. 1. As stated previously, 100 pounds of impurities are initially present in the system. One-half of the impurities may be purged prior to crystallization, leaving 50 pounds of impurities (col. D, line 31). After the first crystallization, there are 5 pounds of impurities left in the crystals (col. D, line 34) and 49 pounds of mother liquor (col. D, line 35). The mother liquor is purged from the system.

Next, the crystals and impurities from the first crystallization are recrystallized. The total feed to the system is 5 pounds of crystals and impurities (col. D, line 37), which was produced by the first crystallization. The recrystallization yields 1 pound of impurity in the crystals (col. D, line 38) and 5 pounds of mother liquor (col. D, line 39). The mother liquor is recycled and the total feed is 55 pounds (col. D, line 33). The overall impurity removal is 98.90% (col. D, line 48). Hence, although the percentage of impurities removed is the same as when the impurities are not removed prior to crystallization, the sucralose yield is much greater. This effect is more pronounced with further crystallization steps as shown in FIG. 1, columns E, F, and G.

In column E, no impurities are purged before crystallization and the feed is initially crystallized and the resulting mother liquor is purged as described above. The first crystallization is followed by three subsequent recrystallizations where the resulting mother liquor is recycled. This process yields a 9% recovery of sucralose (col. E, line 28) and results in overall impurity removal of 99.99% (col. E, line 48). The process used in Column F is the same as in column E, except that one-half of the impurities are removed before any crystallization. This process yields a 17% recovery of sucralose (col. F, line 28) and an overall impurity removal of 99.99% (col. F, line 48), which is an improvement of 186% over the process without an impurity purge (col. F, line 29).

Further, if 75% of impurities are purged before any crystallization step, the recovery of sucralose is even greater (col. G). Removing 75% of impurities through extraction before crystallization yields a recovery of 25% of sucralose (col. G, line 28) and an overall impurity removal of 99.99% (col. G, line 48). This analysis shows that an improvement in overall sucralose recovery can be effected by purging impurities prior to crystallization.

Purification by Crystallization

Purification of sucralose by crystallization may be an iterative process including preparing a saturated or supersaturated solution of sucralose, exposing the solution to conditions that permit crystallization (which may include the addition of seed crystals), harvesting the crystals so obtained, then re-dissolving these crystals followed by concentration to render the solution saturated or supersaturated, and allowing crystal formation to occur. In one embodiment, each crystallization step may improve the purity of sucralose by about 2 to about 5 times that of the starting material at that step.

FIG. 2 shows that increasing the number of crystallizations does not negate or mitigate the effect of a non-crystalline extraction (i.e., purging impurities). For example, in the process utilized to create the data in FIG. 2, the feed to the system was crystallized once, recrystallized three more times, followed by recrystallization of the mother liquor, for a total of five crystallizations. Indeed, three, four, five or more than five sequential or non-sequential crystallizations are contemplated within the scope of the methods of the present invention. The basic process used was the same process as used in FIG. 1, with the exception that crystallization of the mother liquor was performed. However, the effect of the initial non-crystalline extraction is still pronounced. Specifically, the overall recovery of sucralose is 27% for a total of five crystallizations when no impurities are purged through a non-crystalline extraction (col. D, line 32). When 50% of the impurities are purged using a non-crystalline extraction before crystallization, the overall recovery of sucralose increases to 39% (col. E, line 32). Further, if 75% of the impurities are extracted prior to crystallization, the overall recovery of sucralose is 48% (col. F, line 32).

FIGS. 3a and 3b show the same trend. Referring to FIG. 3a, the number of crystallizations is increased. As in FIG. 2, the feed to the system was crystallized once; however, the feed was then recrystallized five more times and the mother liquor was also recrystallized for a total of seven crystallizations. As before, the effect of the non-crystalline extraction can still be shown. However, the effect of the initial non-crystalline extraction is still pronounced. Specifically, the overall recovery of sucralose is 18% for a total of seven crystallizations and when no impurities are purged through a non-crystalline extraction (col. J, line 47). When 50% of the impurities are purged using a non-crystalline extraction before crystallization, the overall recovery of sucralose increases to 32% (col. K, line 47), which is an improvement of 180% over the process without an impurity purge (col. K, line 48).

Increasing Yield by Recycling Mother Liquors

The effectiveness of a non-crystallization extraction step in improving overall yield may be enhanced by recycling the mother liquors from one or more of the subsequent crystallization steps to the feed solution for the extraction step. These mother liquors may concentrate the impurities remaining after crystallization, and recycling of these solutions to the extraction phase may allow the efficient removal of these impurities without sacrificing overall recovery.

One skilled in the art will readily perceive that overall yield of the sucralose and the purity of the sucralose obtained may be modulated by careful design of the flow sequence for recycling the mother liquors. For example, a mother liquor with a relatively high impurity level may most effectively be processed by returning the mother liquor to the feed stream of the initial non-crystallization extraction. Additionally, mother liquor with a high impurity level may also be subjected directly to the non-crystallization extraction, without being combined with another feed stream. Alternatively, a mother liquor with a low impurity level may be recycled to an upstream crystallization step, where the relatively low impurity level may not impair either the rate of crystallization or the purity of the crystals produced (in fact, if the impurity level of the mother liquor is less than that of the feed solution to which it is added, the rate of crystallization and the purity of the crystals obtained may be enhanced).

In one aspect of the present invention, the recovery of sucralose may be improved by concentrating and recrystallizing the mother liquor that remains from a crystallization step after the crystals have been removed. This may be done at each crystallization or recrystallization step. Mother liquor from the first step remains a problem, but may be treated by concentration and, if the impurities allow, recrystallization. The sucralose remaining in the mother liquor after crystallization has been completed may most effectively be recovered by recycling the mother liquor to the initial non-crystallization extraction step.

Referring to FIG. 4, one embodiment of a typical mother liquor recovery scheme is shown. First, crude sucralose solution 100 may be fed to first crystallizer 150. After crystallization, crystals 200 and remaining mother liquor 300 may be separated. The separated mother liquor 300 may be concentrated by a mother liquor concentrator 350 and resultant stream 400 may be fed to a second crystallizer 450. Crystals 500 from second crystallizer 450 may then be mixed with those from first crystallizer 150 to create total product 600. Stream 700, the mother liquor from second crystallizer 450, may be the net impurity purge from the system. Because crystals 500 may come from a mother liquor with a higher impurity level than the first crystallizer, they may be less pure than crystals 200.

Figure 5:
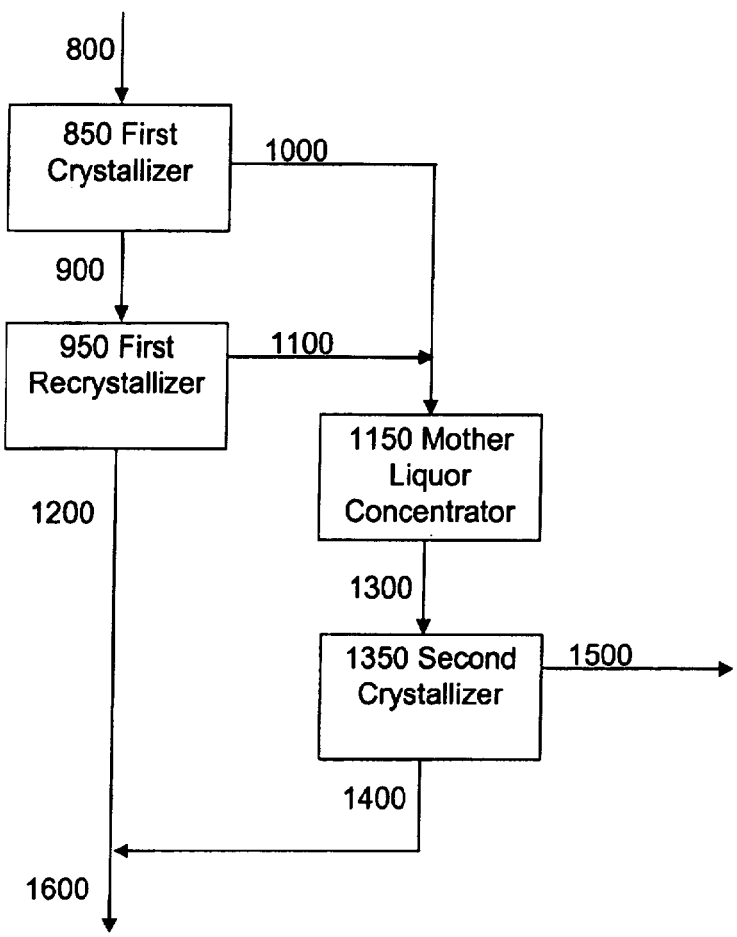
FIG. 5 provides a flowchart of a method in which mother liquors from multiple crystallization steps are combined prior to concentration and recrystallization.

FIG. 5 depicts another embodiment in which a combined stream of all the mother liquors from the various steps is utilized. Crude sucralose 800 may be fed to first crystallizer 850. After crystallization, crystals 900 and remaining mother liquor 1000 may be separated. Crystals 900 may then be fed to first recrystallizer 950. After recrystallization, crystals 1200 and remaining mother liquor 1100 may be separated. Mother liquors 1000 and 1100 may be concentrated by mother liquor concentrator 1150 and the resultant stream 1300 may feed second crystallizer 1350. Crystals 1400 from second crystallizer 1350 may be mixed with crystals 1200 from first recrystallizer 950 as total product 1600. Stream 1500, the mother liquor from second crystallizer 1350, may be the net impurity purge from the system. Because crystals 1400 may come from a mother liquor with a higher impurity level than the first recrystallizer, they may be less pure than stream 1300. Likewise, crystals 1200 may be purer than stream 900 as they may come from a purer feedstock.

Figure 6:
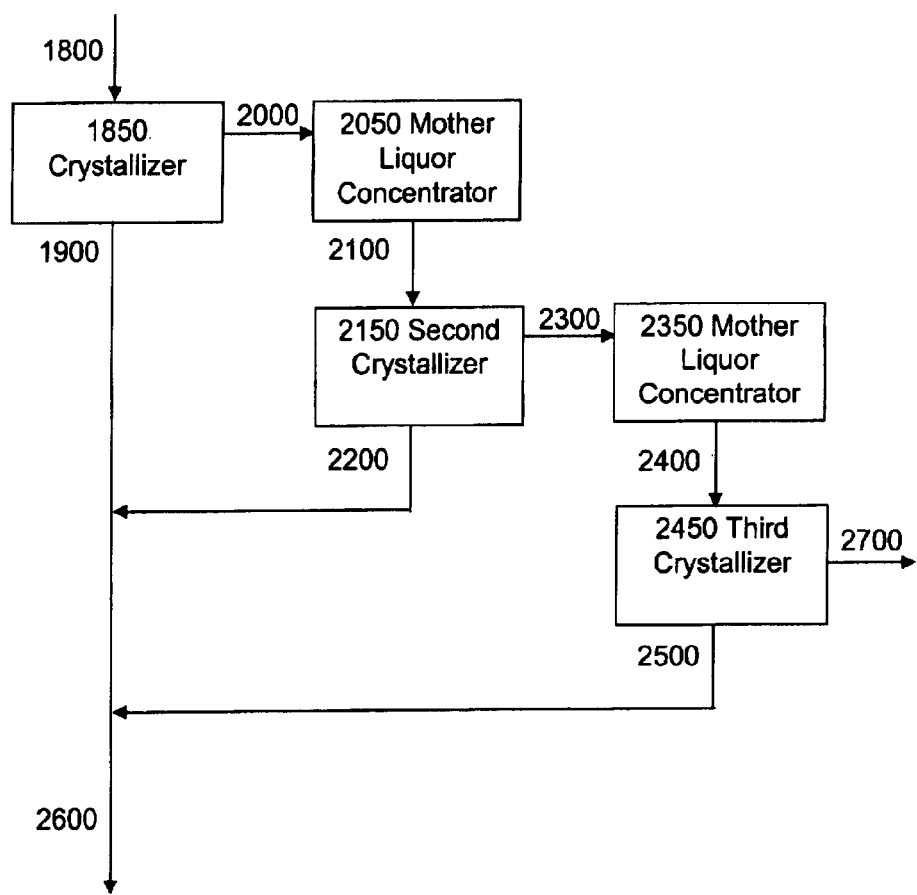
FIG. 6 provides a flowchart of a multiple cropping mother liquor recovery method in which mother liquor is subjected to sequential operations of concentration and crystallization.

FIG. 6 depicts an example where a multi-crop mother liquor may be recovered, i.e., concentration and recrystallization of multiple mother liquors from previous mother liquor concentrations and recrystallizations. In this depiction, crude sucralose 1800 may be fed to first crystallizer 1850. After crystallization, crystals 1900 and remaining mother liquor 2000 may be separated. Mother liquor 2000 may be concentrated in mother liquor concentrator 2050 and the resultant stream 2100 may be fed to second crystallizer 2150. After crystallization, mother liquor 2300 from second crystallizer 2150 may be concentrated by mother liquor concentrator 2350 into stream 2400, which may be fed to third crystallizer 2450. Crystals 2200 from second crystallizer 2150 and crystals 2500 from third crystallizer 2450 may be mixed with crystals 1900 from first crystallizer 1850 as total product 2600. Stream 2700, the mother liquor from third crystallizer 2450 may be the net impurity purged from the system.

Figure 7:
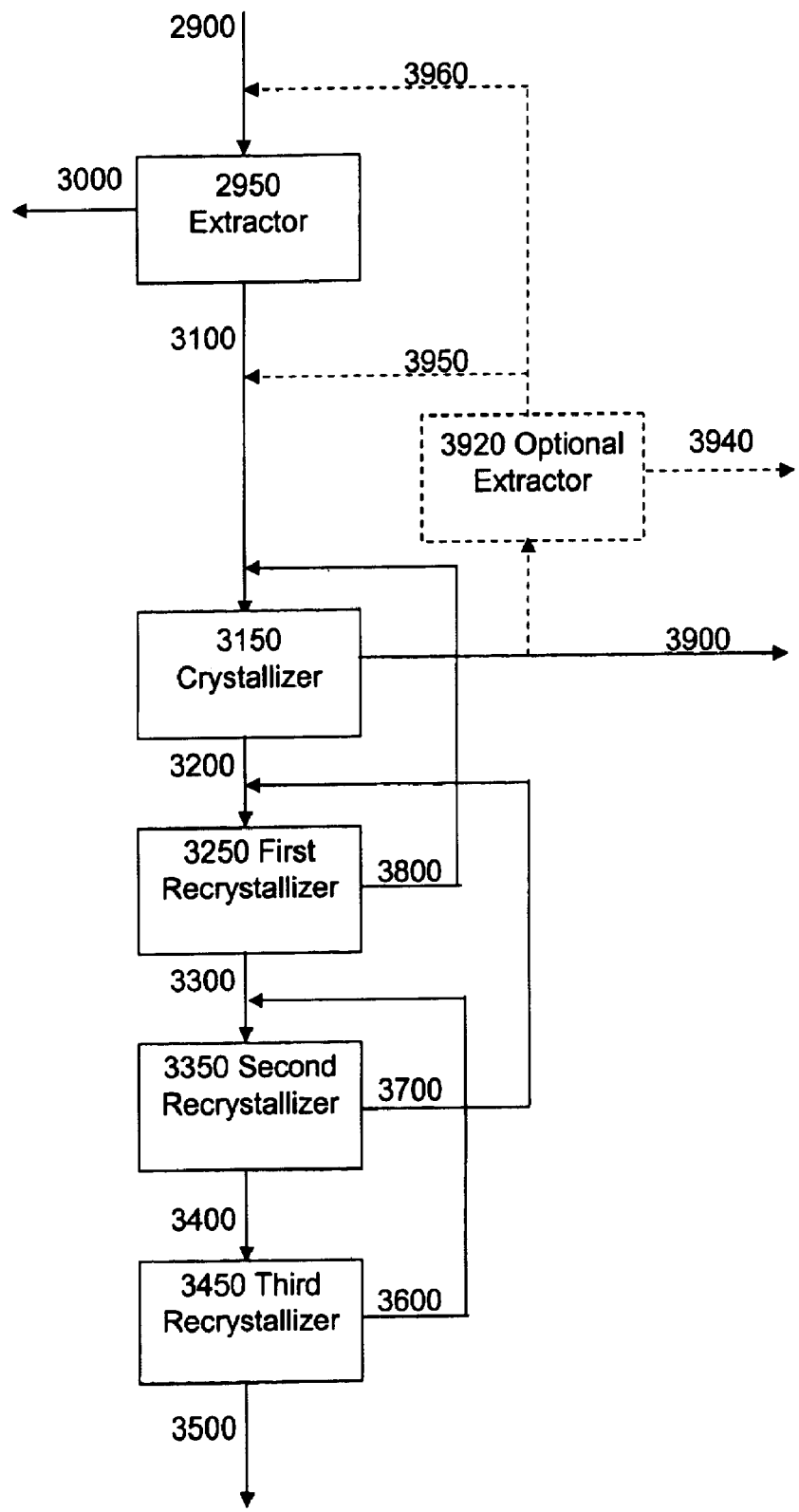
FIG. 7 provides a flowchart of several preferred approaches for the recovery of sucralose or partially blocked sucralose precursors.

FIG. 7 shows another specific embodiment for combining solvent extraction, crystallization extraction, and recycling of mother liquors. In this approach crude sucralose 2900 may be fed to liquid-liquid extractor 2950. Such extractors and extractive processes are known to those skilled in the are and are described in detail above. Typically sucralose may make up less than or about 50% of the chlorinated carbohydrates in a crude sucralose stream. In this method, resultant stream 3100 may not achieve the required finished product sucralose purity, but may provide high sucralose recovery, so as to maintain the overall efficiency of the method, as well as providing a significant reduction in impurities: specifically, unwanted chlorinated carbohydrates. This approach may provide significant improvements in the potential yield of the resultant purification. Unwanted carbohydrates may be purged into stream 3000. Preferably, other non-carbohydrate impurities remaining from the previous synthetic steps may also be purged.

Crystals 3200, 3300, 3400, and 3500 are crystals from first crystallizer 3150, first recrystallizer 3250, second recrystallizer 3350, and third recrystallizer, 3450, respectively. Streams 3600, 3700, and 3800 represent mother liquors from third recrystallizer 3450, second recrystallizer 3350, and first recrystallizer 3250, respectively, and may be recycled into streams to be crystallized to enhance the recovery. Stream 3900 represents the net purge from the crystallization system. There may also be an optional extractor 3920 that extracts impurities from purge 3900. If a second extractor 3920 is used, impurities 3940 may be extracted and purged. The resulting, purer stream may be recycled in path 3950 into first crystallizer 3150 or may be extracted again by extractor 2950 in path 3960.

If the optional first crystallization mother liquor impurity extraction shown in FIG. 7 is employed, the recovery of sucralose may improve as compared to recrystallization without recycling the mother liquors; however, the impact of the removal of impurities may remain the same. Again, FIGS. 1, 2, and 3 show the increased importance of the pre-crystallization removal of impurities as higher purification levels are desired. Note that the sucralose recovery may be improved well over 100% if impurities are purged prior to crystallization.

Referring again to FIG. 7, process stream 3940 may be the purge from the optional extraction and stream 3950 may be the recycled, purified first mother liquor stream. This effect may be enhanced by recycling the mother liquors from the optional extraction step upstream of the pre-crystallization extraction step (process stream 3960 in FIG. 7). Recycling the mother liquors in this manner may allow the efficient removal of impurities from the streams which have concentrated the impurities without sacrificing recovery.

Figure 8:
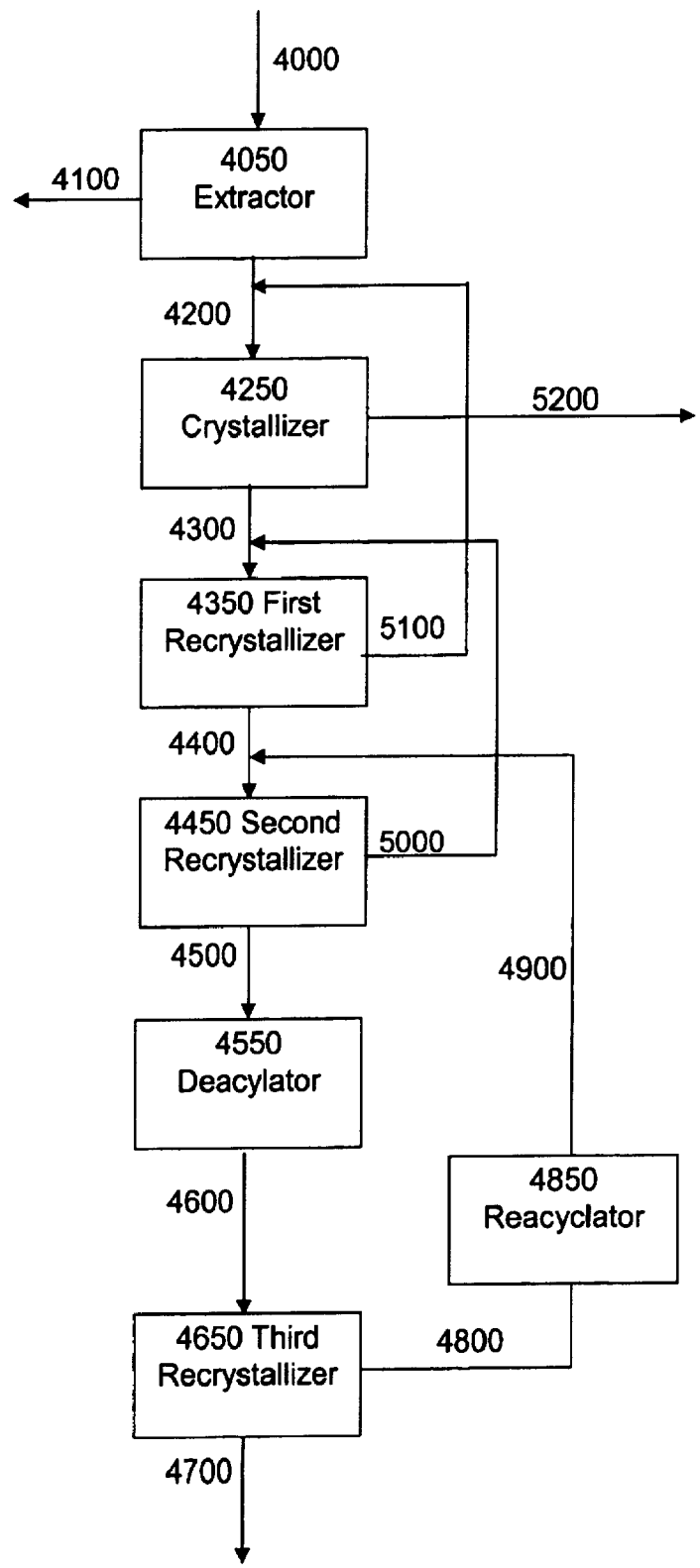
FIG. 8 provides a flowchart of a method for purifying an acylated or otherwise substituted sucralose precursor by crystallization with recycling of the mother liquor, followed by removal of the blocking group and additional crystallization.

The same technique may be applied to the purification of sucralose precursors, and to mixed processes where some of the purification occurs at the precursor stage and some purification occurs after the final reaction to make sucralose. FIG. 8 shows still another embodiment. In this example, three crystallizations may be used prior to conversion of the sucralose precursor to sucralose, and one recrystallization may follow the conversion. However, the total number of crystallizations and the number performed before and after deacylation are not critical.

In FIG. 8, a crude sucralose precursor 4000, such as acylated sucralose, for example, may feed a liquid-liquid extractor 4050. In a specific embodiment, an ethyl acetate/water system may be used for the extraction. A typical crude sucralose precursor may comprise less than 50% of the chlorinated carbohydrates in a crude sucralose precursor stream. Unwanted carbohydrates are purged into stream 4100. The extracted solution 4200 is then crystallized in crystallizer 4250. As in the previous discussion, the resultant crystals 4300 do not need to achieve the final required equivalent sucralose purity of the precursor. Similarly, a significant reduction in other chlorinated sucralose precursors with minimal loss of the sucralose precursor may be preferable.

After the extraction step a multiple recrystallization scheme, or any equivalent scheme, with recycled mother liquors may be used to further purify the sucralose precursor. Streams 4300, 4400, and 4500 are crystals from each of the subsequent crystallizations, and streams 5000 and 5100 represent the mother liquors from these steps being recycled back to enhance the recovery. Stream 5200 may represent the net purge from the crystallization system. The crystals from the final sucralose precursor crystallization 4500 may be fed to a deacylator 4550 to convert the partially purified sucralose precursor to sucralose. The resultant stream 4600 may then be crystallized to produce sucralose crystals of high purity 4700. In this example, the mother liquor 4800 from this step may be reacylated by a reacylator 4850 by, for example, the methods of U.S. Pat. No. 5,298,611, to produce stream 4900, which may be recycled back into the process to be recrystallized.

The purification of the sucralose may also be expressed as a ratio of purified sucralose to other impurities or other chlorinated sucrose derivatives. FIG. 9 provides an exemplary analysis of the purified sucralose of the present invention. FIG. 9 provides the lot number, the adjusted assay value, and various impurities, which may be categorized as chlorinated impurities and other impurities. Residue on ignition may be defined as unvaporized inorganic matter from the assay. All impurities are in percentages. There are two columns of ratios in the table. The ratio of sucralose to all of the impurities was calculated by adding the individual values associated with each impurity for each lot, dividing by 100, and inverting the result. For example, to calculate the ratio of sucralose to all impurities for lot SCN 412, the following values were added together: water (0.06), residue on ignition (0.01), 4,6'-dichlorogalactosucrose (0.01), 4,1'-dichlorogalactosucrose (0.01), 1',6'-dichlorosucrose (0.01), 3',6'-anhydro-4,1-dichlorogalactosucrose (0.01), 1',6'-dichlorosucrose (0.01), 3',6'-anhydrp-4,1-dichlorogalactosucrose (0.01), 4,1',6'-trichlorogalactosucrose-6-acetate (0.01) 6.1',6'trichlorosucralose (0.01), and unknown chlorinated carbohydrates (0.01), divided by 100, and then inverted. Likewise, the ratio of sucralose to chlorinated impurities may be calculated by adding the values for the chlorinated impurities together, dividing by 100, and inverting the result. As shown below, the ratio of impurities to sucralose ranges from approximately 500:1 (all impurities) to approximately 1400:1 (chlorinated impurities), specifically 556:1 to 1428:1. Notably, many of the impurities listed in the chart are less than 0.01. Accordingly, in determining the ratios, these values were rounded to 0.01. Consequently the actual ratios of sucralose to impurities may be much greater, depending upon the resolution of the test.

Other methods known in the art may also be used to characterize the purified sucralose compositions of the present invention such as, for example, IR spectra or Nuclear Magnetic Resonance ("NMR") spectra. IR spectra may be used to determine the impurities by relating measured infrared spectra of samples to the phase composition thereof so as to relate differences between spectra of the samples to differences in phase composition of the samples; and obtaining the infrared spectrum of a sample of unknown phase composition and comparing the spectrum with the calibration model so as to determine the phase.

NMR entails using a strong static magnetic field employed to line up atoms whose nuclei have an odd number of protons and/or neutrons. A second magnetic field, applied as a pulse transverse to the static magnetic field is then used to pump energy into these nuclei, causing them to precess relative to the static field. After excitation the nuclei gradually return to alignment with the static field and give up the energy in the form of weak but detectable free induction decay (FID) signals. These FID signals are used by a computer to produce spectra that characterize the molecular components of a sample.

A wide range of extraction solvents that have differing solubilities for sucralose and other unwanted compounds, including chlorinated carbohydrates, may be used in the liquid-liquid extractor, such as those described in the U.S. Provisional Application previously mentioned. Likewise, a wide variety of extraction equipment may be used in the scheme, ranging from batch mixer-settlers to continuous multistage countercurrent extractors, as also disclosed in the above referenced provisional application. Finally, it will be clear to those skilled in the art that several physical devices can be used to accomplish the extraction.

In addition, the sucralose preparations obtained by the methodologies of the present invention may be incorporated into a variety of products. Such products include, but are not limited to, beverages, combination sweeteners, consumer products, sweetener products, tablet cores (U.S. Pat. No. 6,277,409), pharmaceutical compositions (U.S. Pat. Nos. 6,258,381; 5,817,340; 5,593,696), rapidly absorbed liquid compositions (U.S. Pat. No. 6,211,246), stable foam compositions (U.S. Pat. No. 6,090,401), dental floss (U.S. Pat. No. 6,080, 481), rapidly disintegrating pharmaceutical dosage forms (U.S. Pat. No. 5,876,759), beverage concentrates for medicinal purposes (U.S. Pat. No. 5,674,522), aqueous pharmaceutical suspensions (U.S. Pat. Nos. 5,658,919; 5,621,005; 5,409,907; 5,374,659; 5,272,137), fruit spreads (U.S. Pat. Nos. 5,397,588; 5,270,071), liquid concentrate compositions (U.S. Pat. No. 5,384,311), and stabilized sorbic acid solutions (U.S. Pat. No. 5,354,902).

Sucralose may also be used to enhance the palatability of a consumer product or beverage. Sucralose may be added to any beverage or consumer product, such as, for example, ice cream, soft drinks, or coffee to enhance palatability. Sucralose is applied to the consumer product or beverage, for example, by spraying or dusting onto or into the consumer product or beverage. More specifically, the consumer product and sucralose may combined and/or blended.

Sucralose may be incorporated within the beverage or consumer product to a level sufficient to enhance the flavor or flavor characteristics of the beverage or consumer product. Further, sucralose may be incorporated within the beverage or consumer product to a level that does not significantly impact the sweetness characteristics of the beverage or consumer product. Specifically, sucralose may be present in the beverage or consumer product at a level of about 3 parts per million to about 0.1% in one embodiment, at a level of about 5 parts per million to about 1000 parts per million in another embodiment, or at a level of about 10 parts per million to about 500 parts per million in yet another embodiment.

EXAMPLES

Without further elaboration, it is believed that one skilled in the art, using the preceding description, can utilize the present invention to the fullest extent. The following examples are illustrative only, and not limiting of the remainder of the disclosure in any way whatsoever.

Example 1

Extraction was combined with crystallization and chromatography to produce a high purity sucralose. Intermediate streams of lower purity were returned to earlier steps in the process to enhance performance as to yield and purity. An initial extraction step produced a discarded aqueous phase and passed a solvent phase forward for crystallization. The non-crystalline portion of the first crystallization was first transferred to an aqueous medium and repurified via chromatography and returned to the feed to the extraction system, thereby purging undesirable materials. An initial aqueous crystallization similarly returned an uncrystallized portion to the same extraction system. Subsequent crystallizations returned their uncrystallized mother liquors to the prior crystallizer. This general scheme has been illustrated in FIG. 7.

Extraction

Feed streams from prior steps in the process (e.g., the synthetic process), the simulated moving bed (SMB) chromatographic purification, and the second (first aqueous) crystallizer were combined to provide a single feedstock. This was concentrated to 2–6% dissolved carbohydrates and fed to a liquid/liquid extraction column (Karr reciprocating extraction column, Koch, Inc., Kansas City, Mo.) in which the solvent (ethyl acetate) was run continuously from the bottom and the aqueous carbohydrate stream fed from the top at one third the feed rate (by mass) of the solvent. The feed was heated to 50° C. to inhibit emulsion formation. The column was agitated at a rate that ensured adequate mixing. The ethyl acetate effluent from the column contained sucralose, and was retained. The aqueous stream contained organic and inorganic impurities and was discarded.

Crystallization

First Crystallizer—Crystallization from Ethyl Acetate

The ethyl acetate effluent was saturated with water. It was dehydrated by being fed into the top of a vigreaux distillation column atop the first crystallizer. The crystallizer was maintained under vacuum and contained the carbohydrate solute dissolved in ethyl aceate. The water was largely removed in this step (final levels 0.1–2%). The water removal decreased the solubility of carbohydrate providing impetus toward crystallization as the solvent was distilled under vacuum. The crystallizer temperature was maintained by circulating the crystalline slurry through a heat exchanger with a centrifugal or diaphragm pump back into the crystallizer, further serving to provide mixing. The crystalline slurry was controlled at a minimum of 39° C. by adjusting the vacuum. The rate of distillation was maintained by adjusting the temperature of the medium heating the heat exchanger. The temperature of the heating medium varied between 42° and 65° C. The upper half of the crystallizer had a diameter twice that of the lower half, with the two portions joined by a conical section, aiding efficient circulation. Feed rate was such as to maintain an average residence time between 2 and 14 hours. Longer average residence times tended to increase yield, but with a corresponding decrease in production rate of the vessel. Slurries were withdrawn by temporarily diverting the output of the circulation pump to an open top basket centrifuge to collect the crystals. The cake on the centrifuge was optionally washed with chilled ethyl acetate containing less than 0.1% water.

The mother liquor was converted by distillation in a rotary evaporator to an organic solvent free aqueous mixture at a carbohydrate concentration of 22% (brix measurement), filtered, and purified chromatographically on a succession of two SMB systems to purge unextractable impurities as shown in U.S. Pat. No. 5,977,349. The product of the first SMB system was reconcentrated via rotary evaporator to 18% solids and purified on a second SMB. The product from the chromatographic purification was reconcentrated to 30% via a rotary evaporator and returned to the previously mentioned extraction feed.

Second Crystallization—Aqueous

The cake from the first crystallizer was dissolved to a concentration of 30% in water at 45°–50° C. or optionally mother liquor from the third crystallizer. This dissolution vessel consisted of an agitated round bottom jacket flask. This was fed to a second crystallizer configured similarly to the first, but lacking the dehydrating column. The capacity of the dissolution vessel was 9 liters instead of 13 liters and the largest diameter of the upper section was only 50% larger than the smaller lower section. Slurry temperature was again maintained at 39° C. A small diaphragm or centrifugal pump was used to maintain continuous circulation through a tube heat exchanger whose temperature was adjusted to control distillation rate. The temperature of the heating medium was maintained below 65° C. and typically at or below 56° C. Average residence time varied between about 3 and about 12 hours. Centrifugation was again accomplished by diverting the recycle stream onto a basket centrifuge at intervals. The centrifuge cakes were either not washed or optionally washed with cold water. The mother liquor was combined in a controlled manner with fresh feed and chromatographically purified material to the previously mentioned extractor.

Third and Fourth Crystallizations—Aqueous

The cake from the second crystallizer was dissolved to a concentration of 30% at 45°–50° C. in water or mother liquor from the fourth crystallizer. This dissolution vessel consisted of an agitated round bottom jacket flask. This was fed to a third crystallizer configured identically to the second. The capacity of the dissolution vessel was 9 liters and the largest diameter of the upper section was only 50% larger than the smaller lower section. Slurry temperature was again maintained at 39° C. A small diaphragm or centrifugal pump was used to maintain continuous circulation through a tube heat exchanger whose temperature was adjusted to control distillation rate. The temperature of the heating medium was maintained below 65° C. and typically at or below 56° C. Average residence time varied between about 3 and about 12 hours. Centrifugation was again accomplished by diverting the recycle stream onto a basket centrifuge at intervals. The centrifuge cakes were either not washed or washed with cold water. The mother liquor was returned to the dissolution vessel prior to the second crystallizer and used to dissolve cake from the first crystallizer.

The fourth crystallizer was 3 liters in volume and was a conventional round bottom flask. Centrifuge cakes from the third crystallizer were dissolved in water at about 45–50° C. This dissolution vessel was agitated and jacketed to maintain temperature. Dissolved sucralose was fed to the fourth crystallizer in a continuous manner to maintain a consistent level in the crystallizer. Crystalline slurry was again circulated by centrifugal or diaphragm pump through a tube heat exchanger with the heating medium temperature used to maintain a consistent rate of distillation. Temperature was controlled to 39° C. by adjusting vacuum. Slurries were periodically diverted to an open top basket centrifuge and either not washed or optionally washed with a small amount of cold pure water. The mother liquor was returned to the dissolution vessel used to dissolve cake from the second crystallizer for addition to the third crystallizer.

Drying

The sucralose crystals from the fourth crystallizer were dried via a fluidized bed dryer from a cake normally containing 5–9% water to less than 2% water. Purities and yields at various steps of the purification process have been described below in Table 2.

TABLE 2

| Process Step | Component or Stream | Load Averages | Carbohydrate Profile (% Sucralose) |
|---|---|---|---|
| Fresh feed from synthesis | | | 65.3% |
| SMB return product | | 22.0% | 78.7% +/− 2.0% |
| E-2 12 stage extractor | Total Recovery | 99.5% +/− 0.1% | 91.3% +/− 0.8% |
| EV-5 E-2 Concentrate | | 7.3% | 91.3% +/− 0.8% |
| First Crystallization | Yield | 84.2% +/− 2.7 | |
| | Slurry concentration | 33.8% +/− 2.9% | |
| | Solids assay | 79.3% +/− 5.5% | 95.8% +/− 0.5% |
| | Mother liquor assay (return to SMB) | 7.3% +/− 1.2% | 72.2% +/− 2.6% |
| Second Crystallization | Yield | 50.5% +/− 3.9% | |
| | Slurry concentration | 51.0% +/− 2.7% | |
| | Solids assay | 89.5% +/− 3.2% | 99.6% +/− 0.3% |
| | Mother liquor assay (Return to extractor) | 36.2% +/− 1.5% | 93.7% +/− 0.7% |
| Third Crystallization | Yield | 48.4% +/− 5.9% | |
| | Slurry concentration | 46.3% +/− 2.9% | |
| | Solids assay | 92.2% +/− 2.4% | 99.90% +/− 0.04% |
| | Mother liquor assay | 32.4% +/− 3.8% | 99.11% +/− 0.39% |
| Fourth Crystallization | Yield | 49.4% +/− 5.7% | |
| | Slurry concentration | 46.0% +/− 2.8% | |
| | Solids assay | 90.5% +/− 2.8% | 99.97% +/− 0.01% |
| | Mother liquor assay | 31.4% +/− 2.4% | not measured |
| Drying solids from last crystallization | Loss on Drying | 6.8% +/− 0.7% | |

Example 2

Figure 10A:
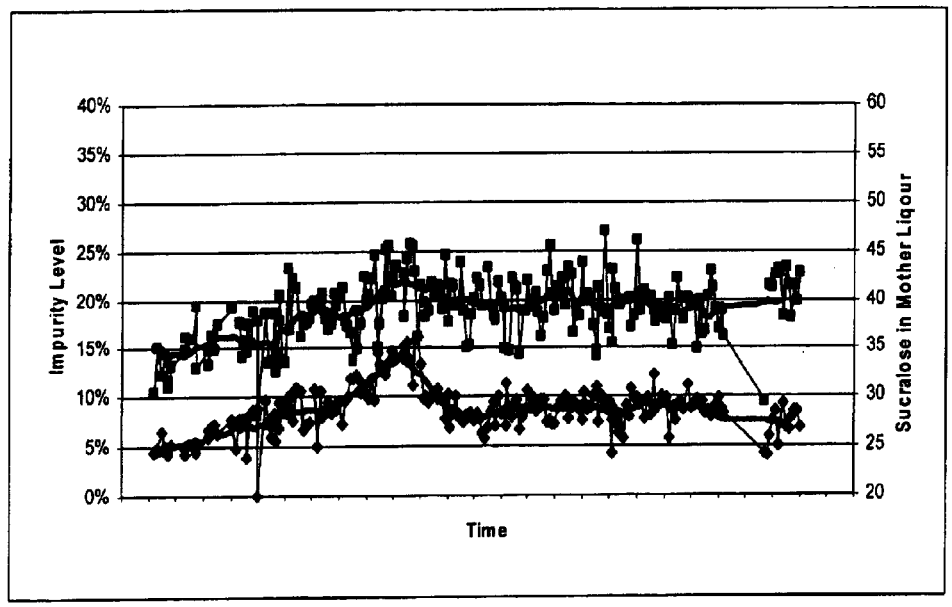
FIG. 10a provides a graph of the effect of impurities on the recovery of sucralose by crystallization.
Figure 10B:
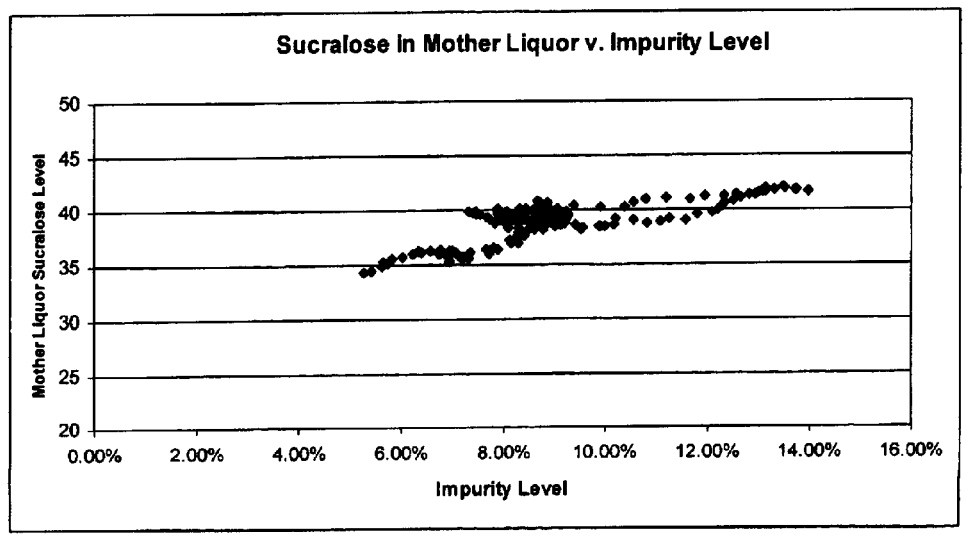
FIG. 10b provides a graph depicting sucralose retained in mother liquor compared to impurity level.
Figure 10C:
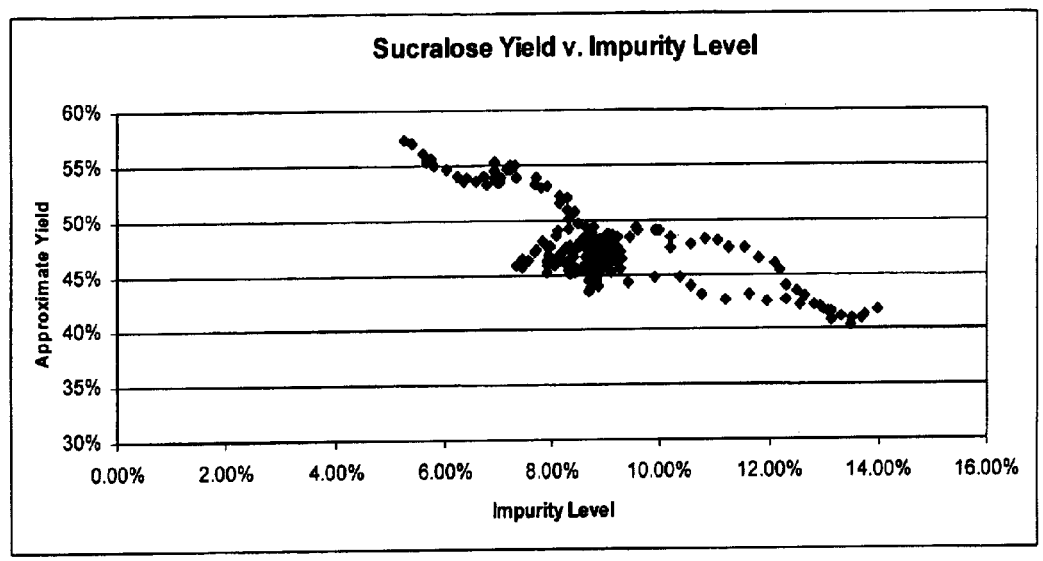
FIG. 10c provides a graph depicting sucralose yield compared to impurity level.

FIGS. 10a–10c present data demonstrating the effects of impurity levels on sucralose crystallization. FIG. 10a presents data from a continuous process crystallization apparatus in which the impurity level of the solution in the apparatus was plotted versus the sucralose remaining in the mother liquor (i.e., the sucralose that was not converted to a crystalline state). This plot shows that the level of sucralose in the mother liquor increased with the impurity level, demonstrating the inhibitory effect of impurities on crystallization. FIG. 10b presents another analysis of these data, again showing that increasing levels of impurities caused a decrease in the crystallization of sucralose. Finally, FIG. 10c shows the effects of impurity levels on the yield from crystallization. Increasing impurity levels over the range of 5% to 14% (weight/weight of solution) had a dramatic effect on the total yield of sucralose from crystallization. As discussed in detail above, FIGS. 1, 2 and 3 present data on the effects of impurity removal at various stages on overall yield and final product purity.

Example 3

Purified sucralose is prepared by the process of solvent-solvent extraction and sequential recrystallizations as shown in examples 1 and 2 of the present invention. Next the taste of the resultant composition is tested in a beverage.

Sucralose solutions are prepared by adding crystalline sucralose to a model soft drink composition that contains 0.14% citric acid and 0.04% trisodium phosphate. The pH of this composition is 3.2. Crystalline sucralose compositions are added to the soft drink composition to yield final levels of 100 parts per million (ppm).

Panelists are selected from the general population, and no specific demographic parameters are utilized in recruiting the panelists. The product samples are prepared and served chilled. Portions are dispensed into individual servings for the panelists. Samples are presented to panelists in a blinded manner (samples are identified only by a random digit label). Each panelist receives three samples for tasting (one sample comprising 100 ppm sucralose and two samples not comprising sucralose), and panelists are given a randomized sequence in which to taste the samples. Thus the order of tasting is completely random. Panelists are asked to select the sample that is different, record that result, record how confident they are of the result, and finally record why the odd sample is different. Between tasting the samples, the panelists are asked to rinse thoroughly with a purified water preparation and take a bite of plain cracker to cleanse the palette. Panelists are also required to wait five minutes before tasting the next sample.

Statistical significance of the correctness of the scores (i.e. panelist ability to detect the sample that is different from the other two) is determined by use of a statistical table that correlates the number of correct responses with a p value.

Panelists are asked to state the reasons for identifying the odd sample and many of the comments made by those panelists choosing the correct sample relate to the increased palatability of the odd sample. A statistically significant difference is found among the samples comprising sucralose and the samples not comprising sucralose with respect to the parameter of palatability, where p is preferably found to be less than or equal to 0.05.

Example 4

Purified sucralose is prepared by the process of solvent-solvent extraction and sequential recrystallizations as shown in examples 1 and 2 of the present invention. Next, sucralose is used to enhance the palatability of a beverage or consumer product.

Thirty persons were placed in a room for two hours with a table displaying two identical serving containers of fruit juice containing the same volume of liquid (FJ1 and FJ2), two identical serving containers of regular cola containing the same volume of liquid (C1 and C2), two identical serving containers of diet cola containing the same volume of liquid (DC1 and DC2), and two identical serving containers of coffee containing the same volume of liquid (CF1 and CF2).

The first serving container of each pair held a beverage comprising 150 ppm of sucralose; the second serving container of each pair held a beverage without sucralose. The volumes within all containers exceeded the volumes that could reasonably be expected to be consumed by the thirty persons within a two-hour time period. Prior to the gathering, the persons were instructed to consume (or not to consume) the beverages in the manner that they would consume the beverages during any other two-hour period.

After the two-hour time period, measurements were taken of the volumes of liquid consumed from each container. The measurements are expressed in units of "volume consumed/two-hour time period." Three different panels of persons are tested.

The averaged measurements pertaining to the fruit juice demonstrated that FJ1 was consumed at a greater rate than FJ2. The averaged measurements pertaining to the cola demonstrated that C1 was consumed at a greater rate than C2. The averaged measurements pertaining to the diet cola demonstrated that DC1 was consumed at a greater rate than DC2. The averaged measurements pertaining to the coffee demonstrated that CF1 was consumed at a greater rate than CF2. These results strongly suggest the preference for the beverages comprising the palatability enhancing composition.

Example 5

Purified sucralose is prepared by the process of solvent-solvent extraction and sequential recrystallizations as shown in examples 1 and 2 of the present invention. Next, sucralose is used to enhance the palatability of a consumer product.

The sucralose is added to one group (1G) of two groups (1G and 2G) of a consumer product such as ice cream to yield final levels of 150 ppm sucralose.

Panelists are selected from the general population, and no specific demographic parameters are utilized in recruiting the panelists. The two groups of samples are prepared and served chilled. Portions are dispensed into individual servings for the panelists. Samples are presented to panelists in a blinded manner (samples are identified only by a random digit label). Each panelist receives two samples for tasting, and panelists are given a randomized sequence in which to taste the samples. Thus, the order of tasting is completely random. In each set of two samples, one sample is from G1 and the other sample is from G2. Panelists are asked to select the sample that tastes the most palatable, record that result and record how confident they are of the result. Between tasting the samples, the panelists are asked to rinse thoroughly with a purified water preparation and take a bite of plain cracker to cleanse the palette. Panelists are also required to wait five minutes before tasting the next sample.

Statistical significance of the correctness of the scores (i.e., panelist ability to detect the most palatable sample) is determined by use of a statistical table that correlates the number of correct responses with a p value.

The results demonstrate that participants deemed the samples comprising sucralose more palatable than the samples not comprising sucralose. A statistically significant difference is found among the samples comprising sucralose and the samples not comprising sucralose with respect to the parameter of palatability, where p is preferably found to be less than or equal to 0.05.

Example 6

Purified sucralose is prepared by the process of solvent-solvent extraction and sequential recrystallizations as shown in examples 1 and 2 of the present invention. Next, sucralose is used to increase the palatability of a beverage.

Four batches of diet soft drink are prepared: DSD1 (containing 0 ppm sucralose), DSD2 (containing 10 ppm sucralose), DSD3 (containing 50 ppm sucralose), and DSD4 (containing 100 ppm sucralose).

Panelists are selected from the general population, and no specific demographic parameters are utilized in recruiting the panelists. Samples from the four batches are prepared and served chilled. Portions are dispensed into individual servings for the panelists. Samples are presented to panelists in a blinded manner (samples are identified only by a random digit label). Each panelist receives four samples for tasting, and panelists are given a randomized sequence in which to taste the samples. Thus, the order of tasting is completely random. In each set of four samples, one sample is from DSD1, one sample is from DSD2, one sample is from DSD3, and one sample is from DSD4. Panelists are asked to select the sample that tastes the most palatable, record that result and record how confident they are of the result. Between tasting the samples, the panelists are asked to rinse thoroughly with a purified water preparation and take a bite of plain cracker to cleanse the palette. Panelists are also required to wait five minutes before tasting the next sample.

Statistical significance of the correctness of the scores (i.e., panelist ability to detect the most palatable sample) is determined by use of a statistical table that correlates the number of correct responses with a p value.

The data indicate that the panelists regard the samples comprising sucralose (namely, the samples from DSD2, DSD3, and DSD4) as more palatable than the samples that do not comprise sucralose (namely, the samples from DSD1). A statistically significant difference is found among the samples comprising sucralose and the samples not comprising sucralose with respect to the parameter of palatability, where p is preferably found to be less than or equal to 0.05.

Example 7

Purified sucralose is prepared by the process of solvent—solvent extraction and sequential recrystallizations as shown in examples 1 and 2 of the present invention. Next, the effect on palatability of a beverage by purified sucralose is tested.

Sucralose solutions are prepared by adding crystalline sucralose to a model soft drink composition that contains 0.14% citric acid and 0.04% trisodium phosphate. The pH of this composition is 3.2. Crystalline sucralose compositions are added to the soft drink composition to yield final levels of 10 ppm sucralose.

A model soft drink composition without sucralose is also prepared.

Panelists are selected from the general population, and no specific demographic parameters are utilized in recruiting the panelists. The product samples are prepared and served chilled. Portions are dispensed into individual servings for the panelists. Samples are presented to panelists in a blinded manner (samples are identified only by a random digit label). Each panelist receives three samples for tasting, and panelists are given a randomized sequence in which to taste the samples. Thus the order of tasting is completely random. In each set of three samples, two are identical in that they do not contain sucralose, and one is different in that it does contain sucralose. Panelists are asked to select the sample that is different, record that result, record how confident they are of the result, and finally record why the odd sample is different. Between tasting the samples, the panelists are asked to rinse thoroughly with a purified water preparation and take a bite of plain cracker to cleanse the palette. Panelists are also required to wait five minutes before tasting the next sample.

Statistical significance of the correctness of the scores (i.e., panelist ability to detect the sample that is different from the other two) is determined by use of a statistical table that correlates the number of correct responses with a p value.

Panelists are asked to state the reasons for identifying the odd sample and a statistically significant number of the comments made by those panelists choosing the correct sample relate to the enhanced palatability of the sample comprising sucralose.

The data indicate that the panelists regard the samples comprising sucralose as more palatable than the samples that do not comprise sucralose. A statistically significant difference is found among the samples comprising sucralose and the samples not comprising sucralose with respect to the parameter of palatability, where p is preferably found to be less than or equal to 0.05.

Though the foregoing description of this invention has focused principally on the purification of sucralose, it will be clear to those skilled in the art that the same techniques can be applied to the purification of sucralose precursors, and to mixed processes where some of the purification occurs at the precursor stage and additional purification occurs after the final reaction to make sucralose. Further, it will be clear that other mother liquor streams may be processed so long as the key features of the invention are practiced (multiple recrystallizations to obtain high purity, with mother liquor recycle to enhance recovery, preceded by use of non-crystallization extraction technology for bulk removal of impurities to prevent impurity-based recovery degradation).

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in industrial chemistry or related fields are intended to be within the scope of the following claims.

What is claimed is:

1. A method of obtaining sucralose from a feed mixture comprising 6-O-acyl-4,1',6'-trichloro-4,1',6'-trideoxygalactosucrose, other chlorinated sucrose byproducts, and optionally other blocked or partially blocked chlorinated sucrose byproducts comprising the steps of:
   (a) purifying said feed mixture to obtain an increased purity sucralose precursor stream containing a total amount of said other chlorinated sucrose byproducts and said other blocked or partially blocked chlorinated sucrose byproducts, relative to 6-O-acyl-4,1',6'-trichloro-4,1',6'-trideoxygalactosucrose, that is lower than a total amount of said other chlorinated sucrose byproducts and said other blocked or partially blocked chlorinated sucrose byproducts, relative to 6-O-acyl-4,1',6'-trichloro-4,1'6'-trideoxygalactosucrose, in the feed mixture; said purifying comprising a non-crystallization extraction step;
   (b) converting said 6-O-acyl-4,1',6'-trichloro-4,1',6'-trideoxygalactosucrose in said increased purity sucralose precursor stream to sucralose;
   (c) crystallizing said sucralose to obtain a crystalline sucralose and a mother liquor; and
   (d) performing at least three additional sequential crystallizations of said crystalline sucralose to obtain a substantially pure sucralose and additional mother liquor.

2. The method of claim 1, said purifying further comprising, after said non-crystallization extraction step, the step of crystallizing 6-O-acyl-4,1',6'-trichloro-4,1',6'-trideoxygalactosucrose to provide the increased purity sucralose precursor stream.

3. The method of claim 1, wherein said crystallizing step is performed three times.

4. The method of claim 1, wherein said crystallizing step is performed four times.

5. The method of claim 1, wherein said crystallizing step is performed five times.

6. The method of claim 1, wherein said crystallizing step is performed more than five times.

* * * * *